US008077945B2

(12) United States Patent
Kawato et al.

(10) Patent No.: US 8,077,945 B2
(45) Date of Patent: Dec. 13, 2011

(54) METHOD OF ANALYZING CELL OR THE LIKE HAVING LINEAR SHAPE, METHOD OF ANALYZING NERVE CELL AND APPARATUS AND PROGRAM FOR PERFORMING THESE METHODS

(75) Inventors: Suguru Kawato, Tokyo (JP); Kenji Mitsuhashi, Tokyo (JP)

(73) Assignee: The University of Tokyo, Tokyo (JP)

( * ) Notice: Subject to any disclaimer, the term of this patent is extended or adjusted under 35 U.S.C. 154(b) by 790 days.

(21) Appl. No.: 12/086,496

(22) PCT Filed: Nov. 13, 2006

(86) PCT No.: PCT/JP2006/322537
§ 371 (c)(1),
(2), (4) Date: Aug. 14, 2008

(87) PCT Pub. No.: WO2007/068856
PCT Pub. Date: Jun. 21, 2007

(65) Prior Publication Data
US 2009/0070089 A1    Mar. 12, 2009

(51) Int. Cl.
*G06K 9/00* (2006.01)
(52) U.S. Cl. ........................................ 382/128; 382/133
(58) Field of Classification Search .................. None
See application file for complete search history.

(56) References Cited

U.S. PATENT DOCUMENTS 7,254,265 B2 *  8/2007  Naske et al. .................. 382/154

FOREIGN PATENT DOCUMENTS

| JP | A 2000-90283 | 3/2000 |
|---|---|---|
| JP | A 2002-207993 | 7/2002 |
| JP | A 2002-312761 | 10/2002 |
| JP | A 2003-9898 | 1/2003 |
| JP | A 2003-14737 | 1/2003 |
| JP | A 2004-70702 | 3/2004 |
| JP | A 2005-95172 | 4/2005 |
| JP | A 2005-525550 | 8/2005 |

OTHER PUBLICATIONS

Santos et al., "A Mathematical Morphology Approach to the Extraction of Nerve Cell Structures," *IEE Conference Publication*, No. 465, pp. 823-826, 1999.

* cited by examiner

*Primary Examiner* — Minh N Tang
(74) *Attorney, Agent, or Firm* — Oliff & Berridge, PLC

(57) ABSTRACT

It is intended to propose a technique whereby a nerve cell is morphologically analyzed automatically based on a three-dimensional image of the nerve cell. First, a dendritic projection is traced by using the scale space method. In this step, irregularities are reduced by using the σ-convolution smoothing method and thus the center line of the dendritic projection is identified. Next, a negative curvature is searched for by the Hess tensor method. The part corresponding to the negative curvature in all coordinate axes is judged as the area occupied by "heads". The center of this area (heads) is referred to as the spine position. Approximation is made on the assumption that the spine head has an ellipsoidal shape. Thus, the minor diameter, medium diameter and major diameter of the ellipsoid are calculated. From the spine position, a perpendicular line is dropped toward the dendritic projection closest thereto and this perpendicular line is considered as the column part. By combining the dendritic projection with the spine head and column thus obtained, the final morphological shape of the nerve cell is obtained.

25 Claims, 16 Drawing Sheets

Spine ANALYSIS BY Neurolucida (1)

(2)

(3)

[FIG. 1]
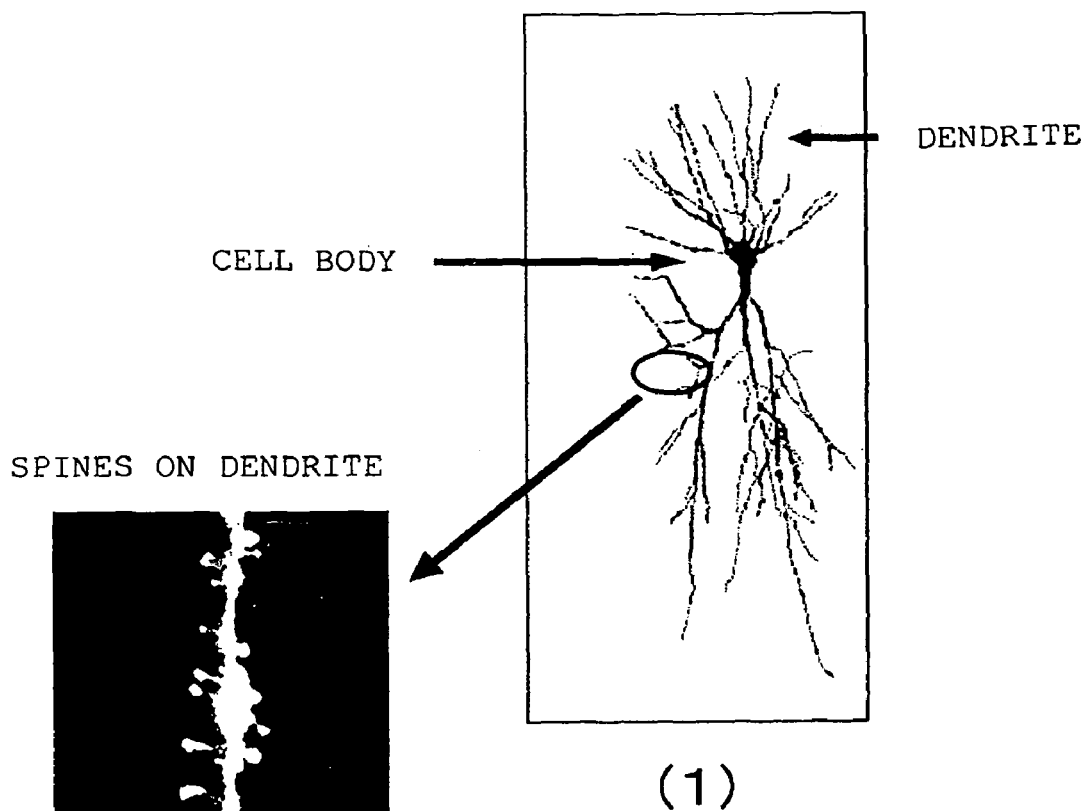
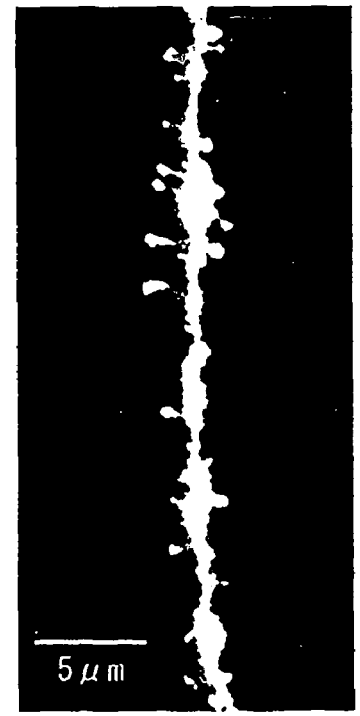

[FIG. 2]
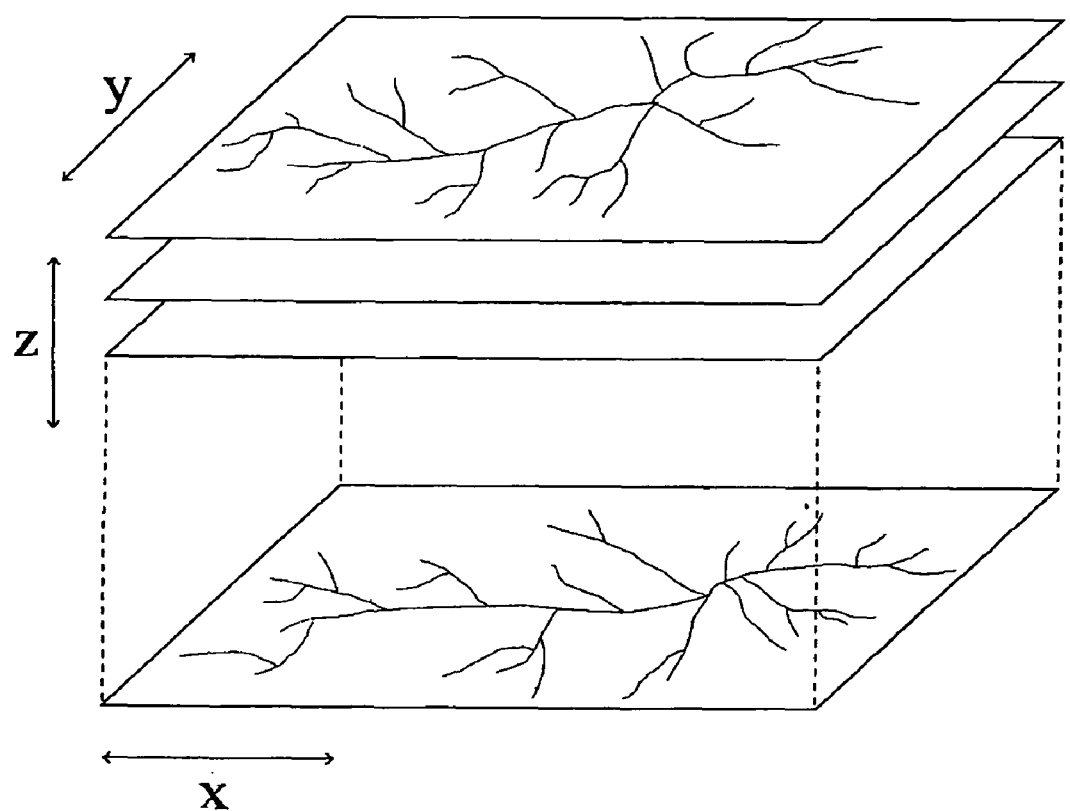
THREE-DIMENSIONAL IMAGE DATA

[FIG. 3]
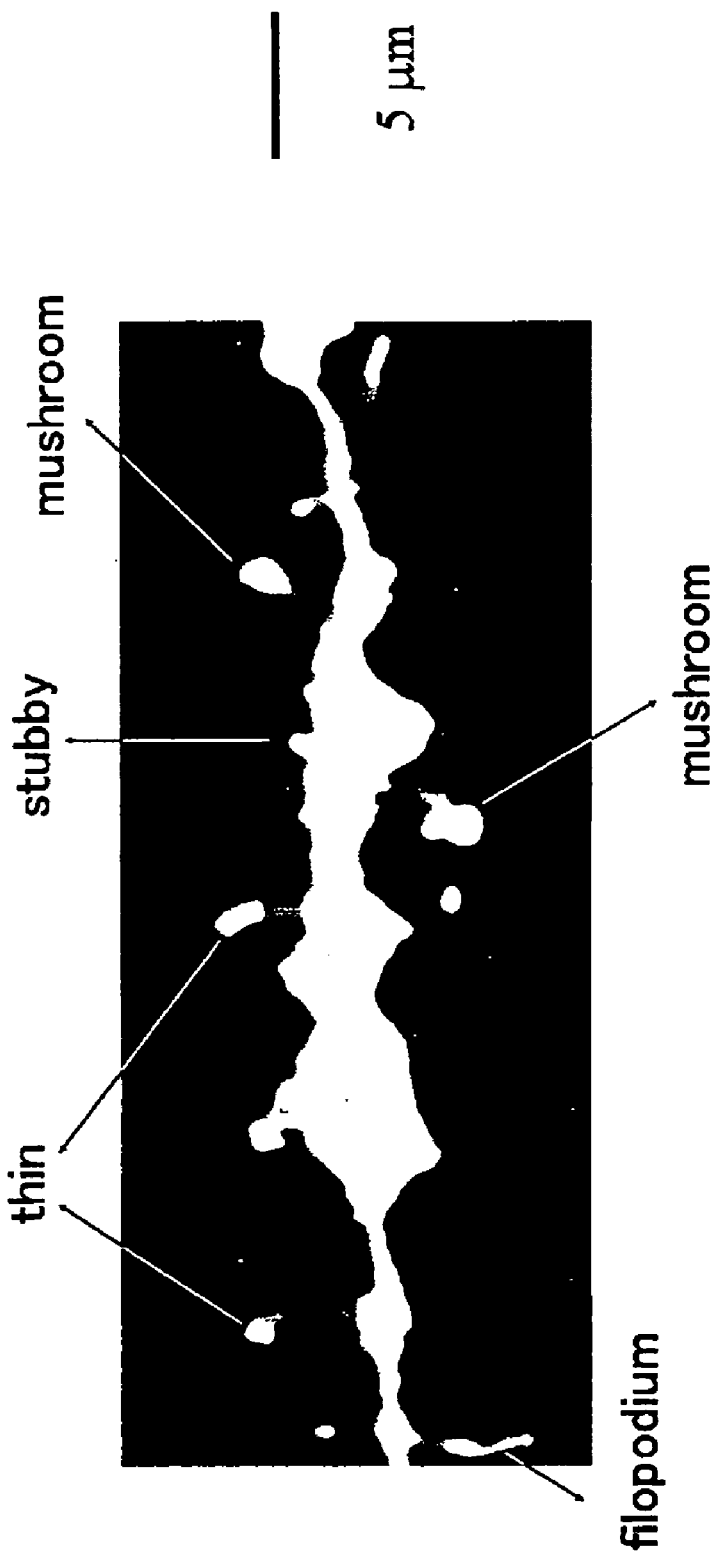

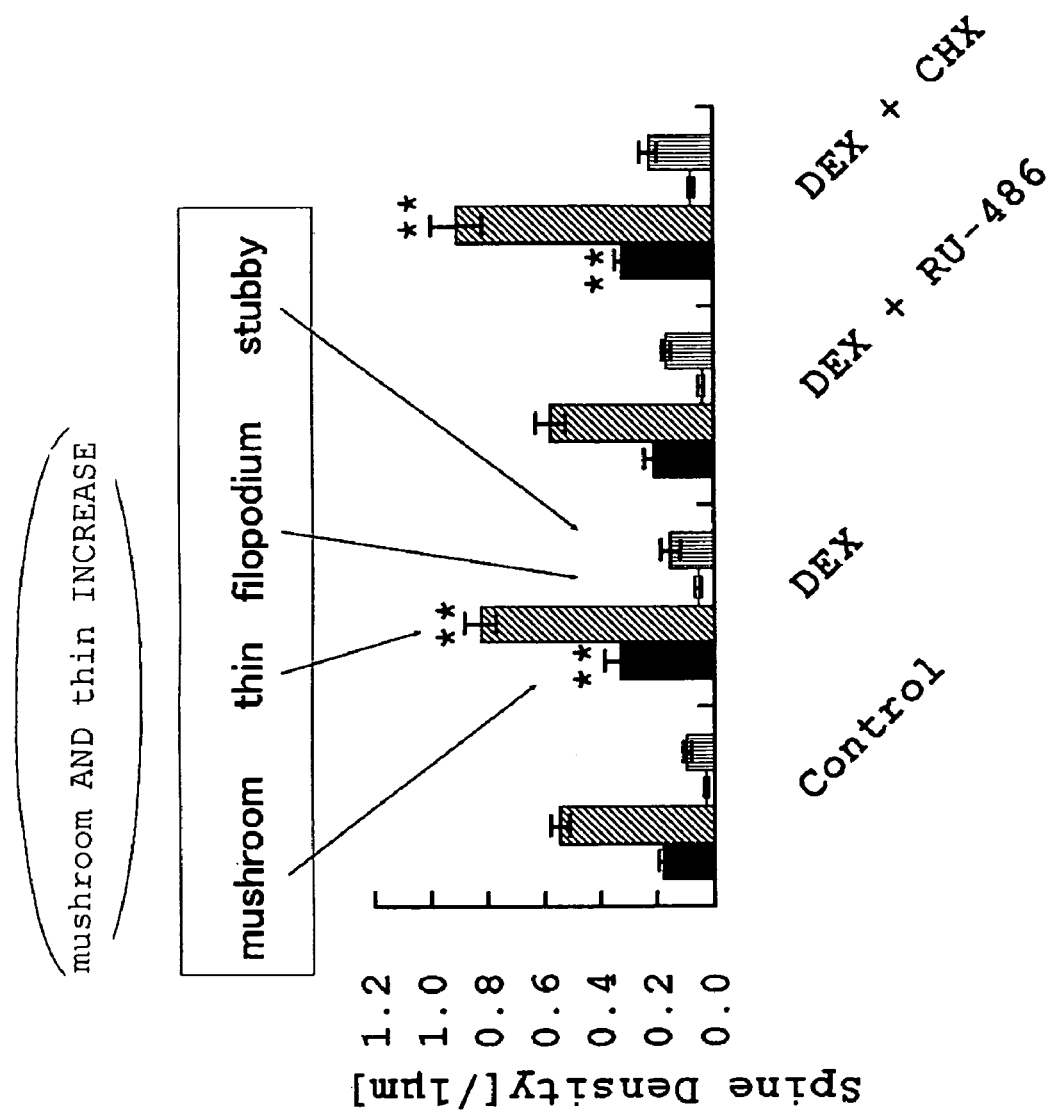
[FIG. 4]

[FIG. 5]
Spine ANALYSIS BY Neurolucida
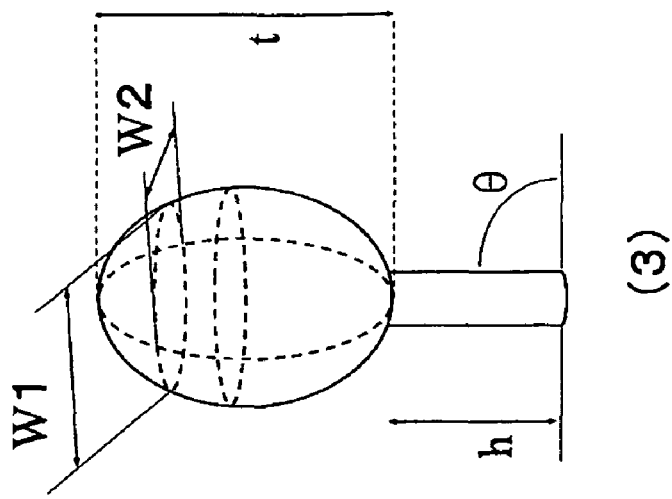
(1)
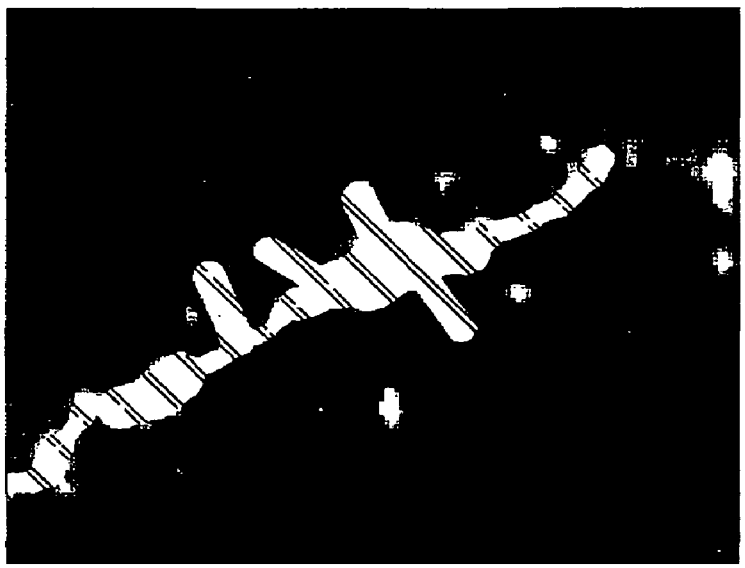
(2)
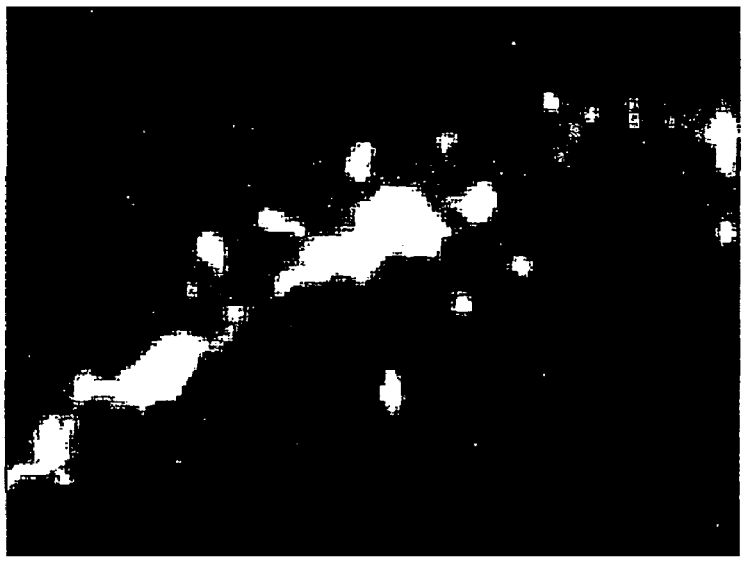
(3)

[FIG. 6]
OPERATIONAL DIAGRAM OF AUTOMATIC IMAGE ANALYZING SOFTWARE
STEP (1) DENDRITE TRACING
STEP (2) DETECTION OF SPINE POSITION
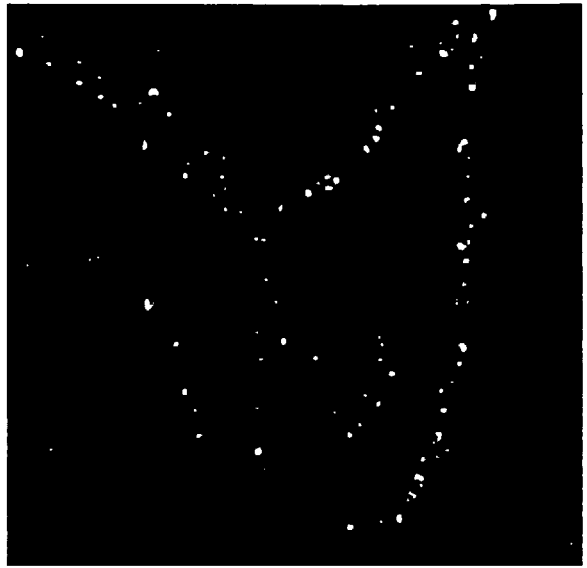
STEP (3) FIT OF SPINE HEAD BY ELLIPSOID
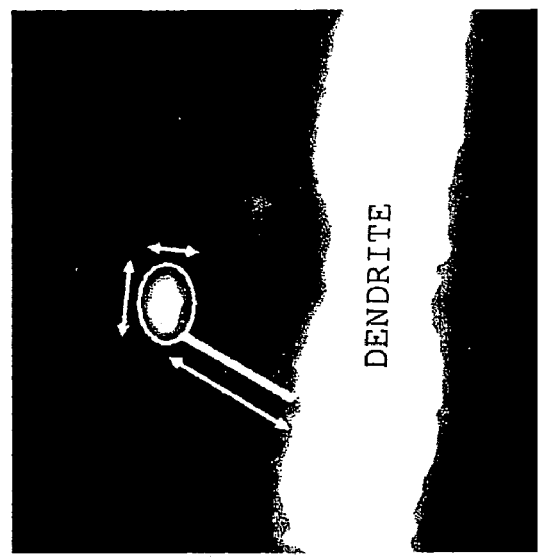

[FIG. 7]
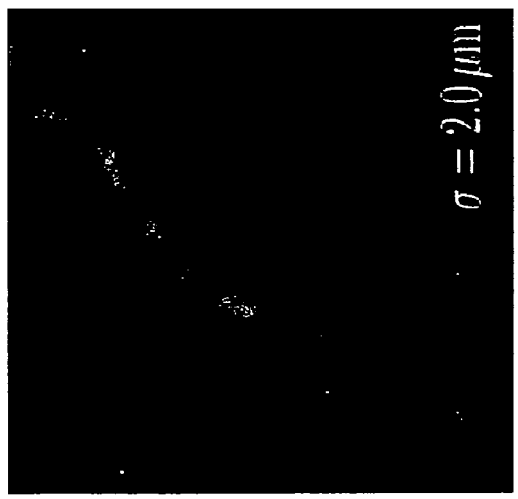
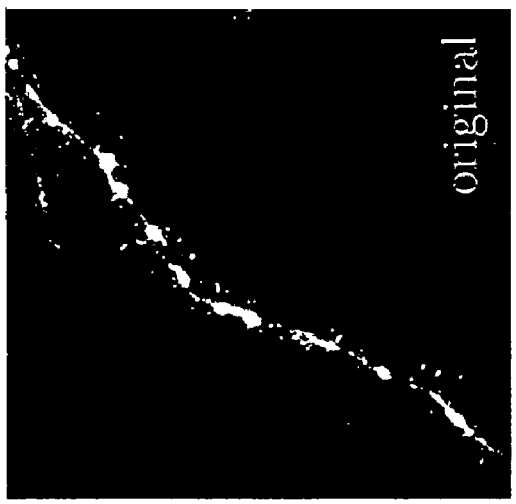
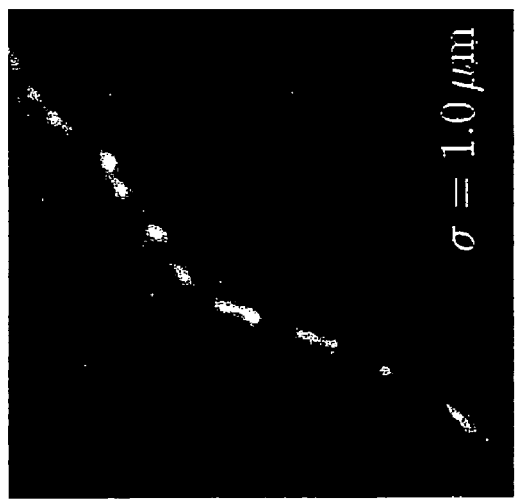

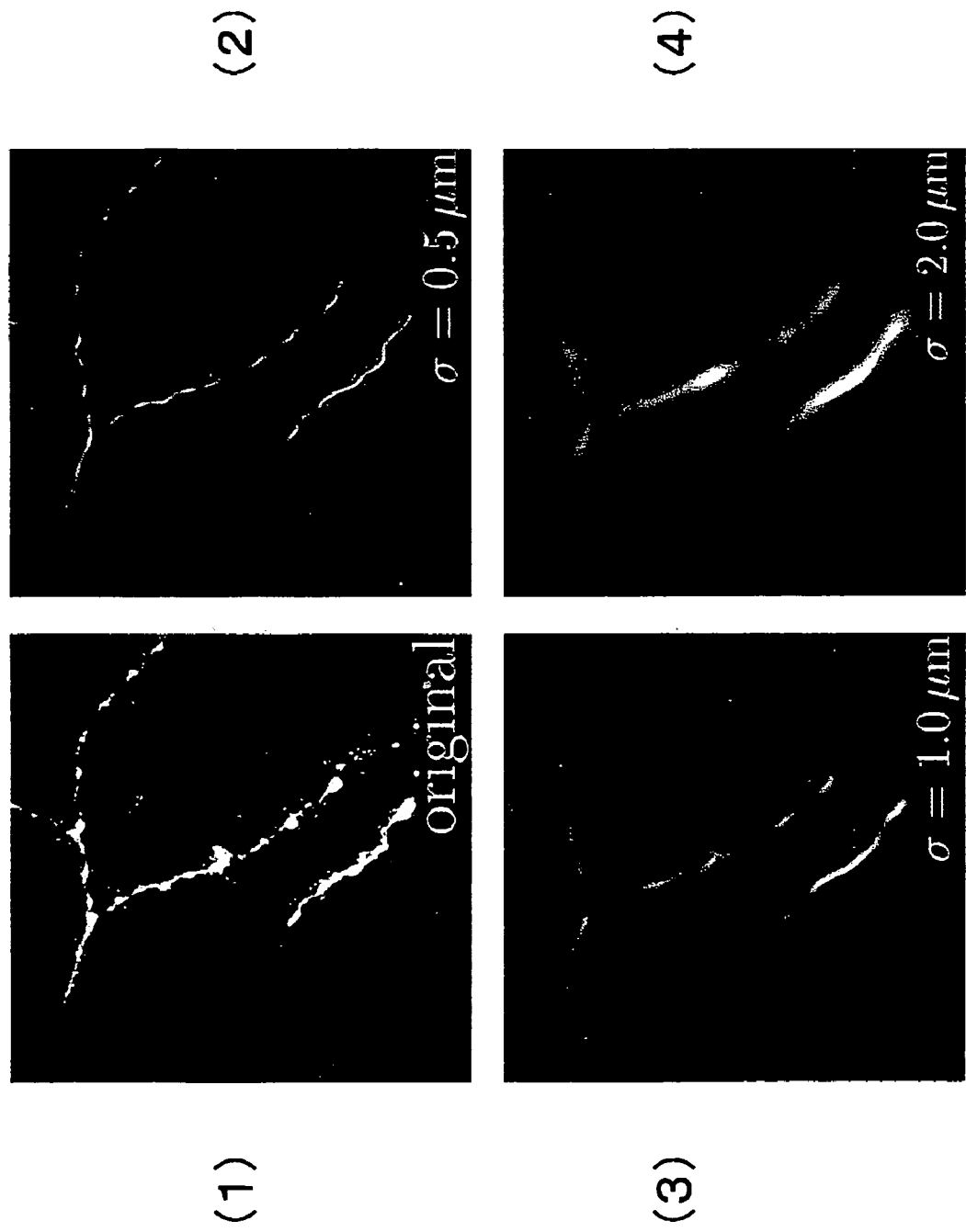
[FIG. 8]

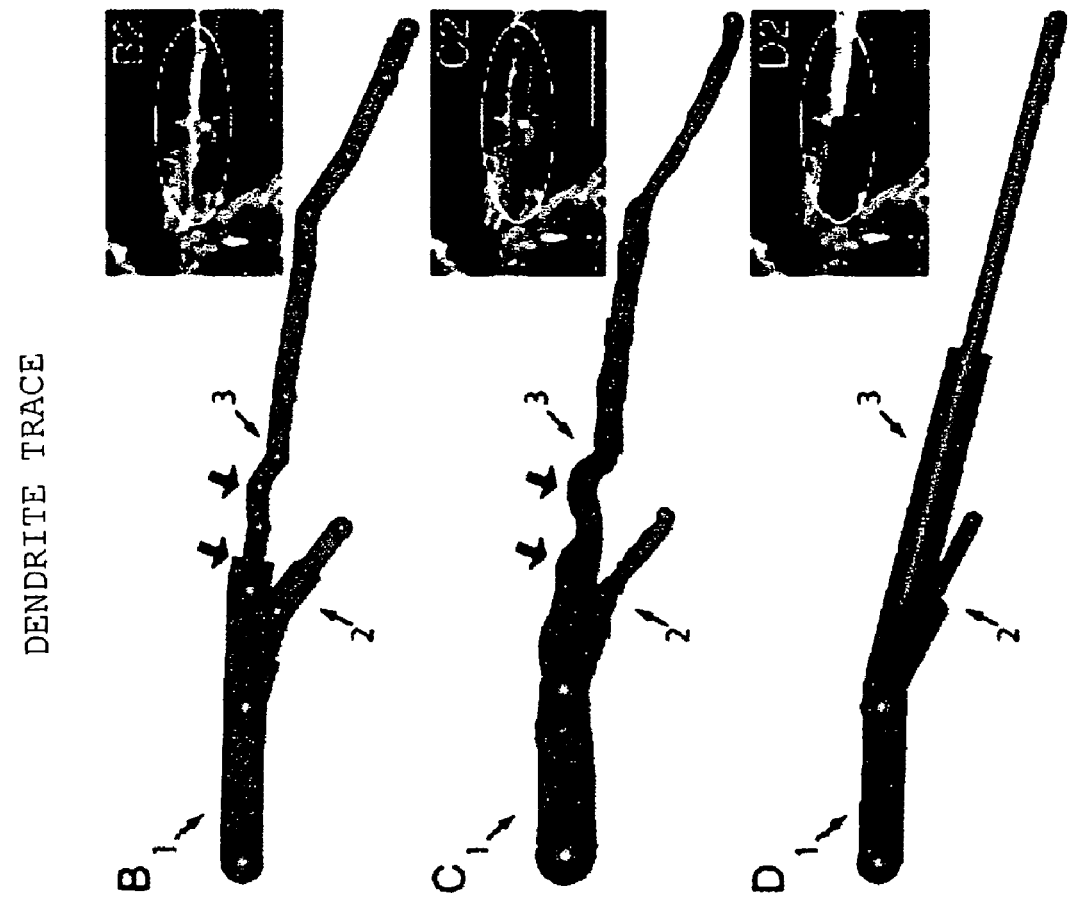
[FIG. 9]

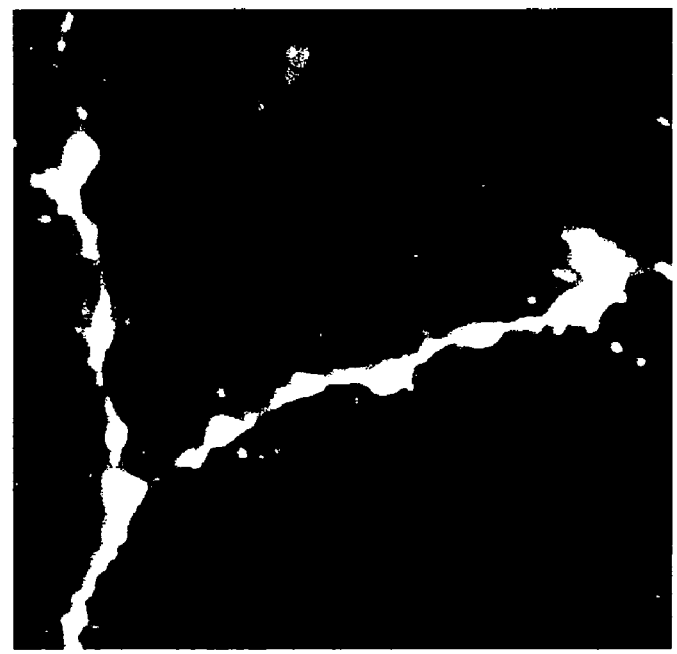
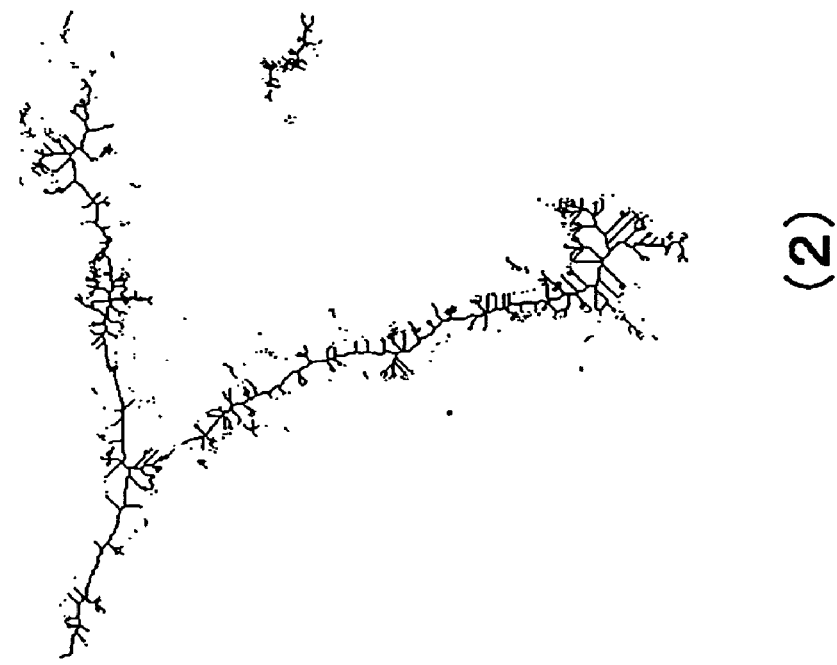
[FIG. 10]

[FIG. 11]
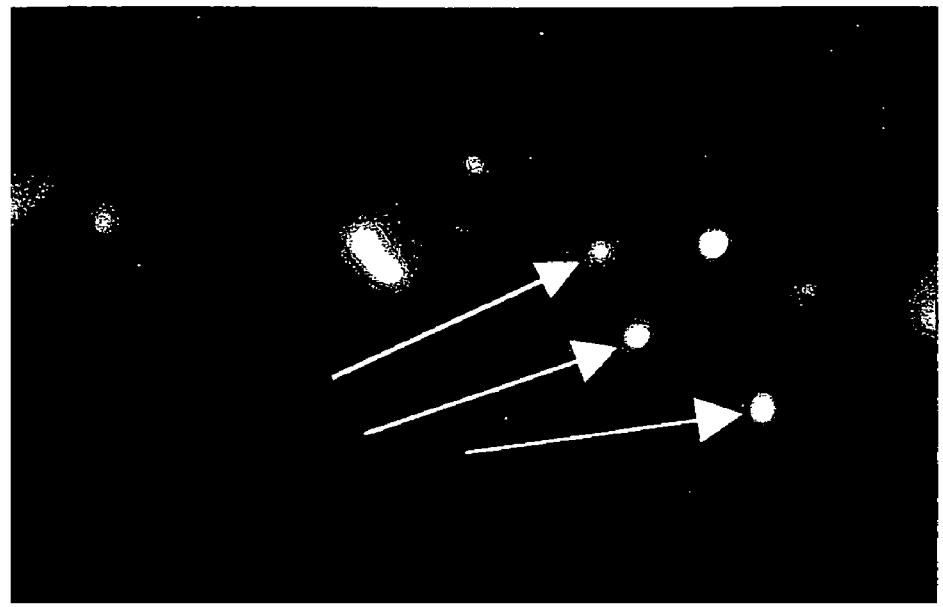
(2)
MAXIMAL VALUE OF $\lambda_1\lambda_2\lambda_3$
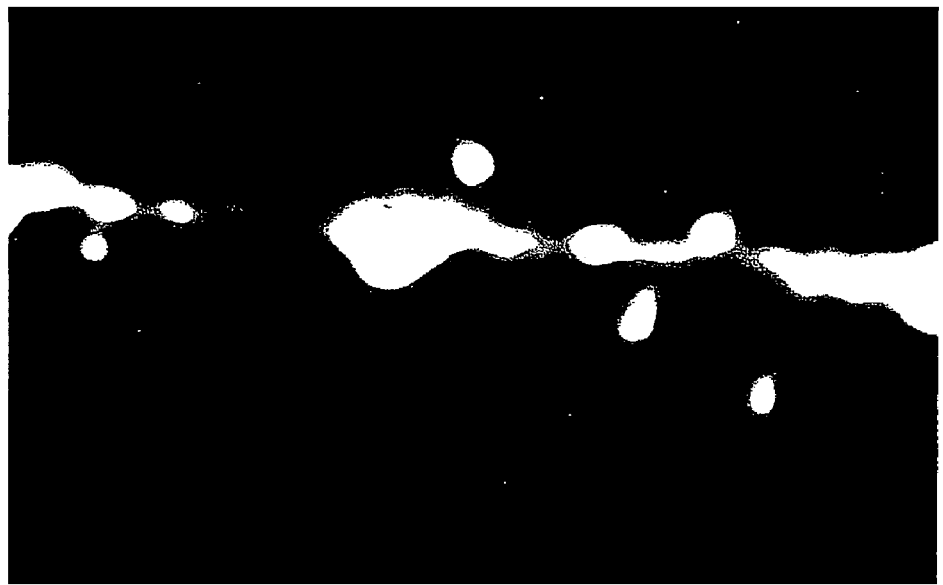
(1)

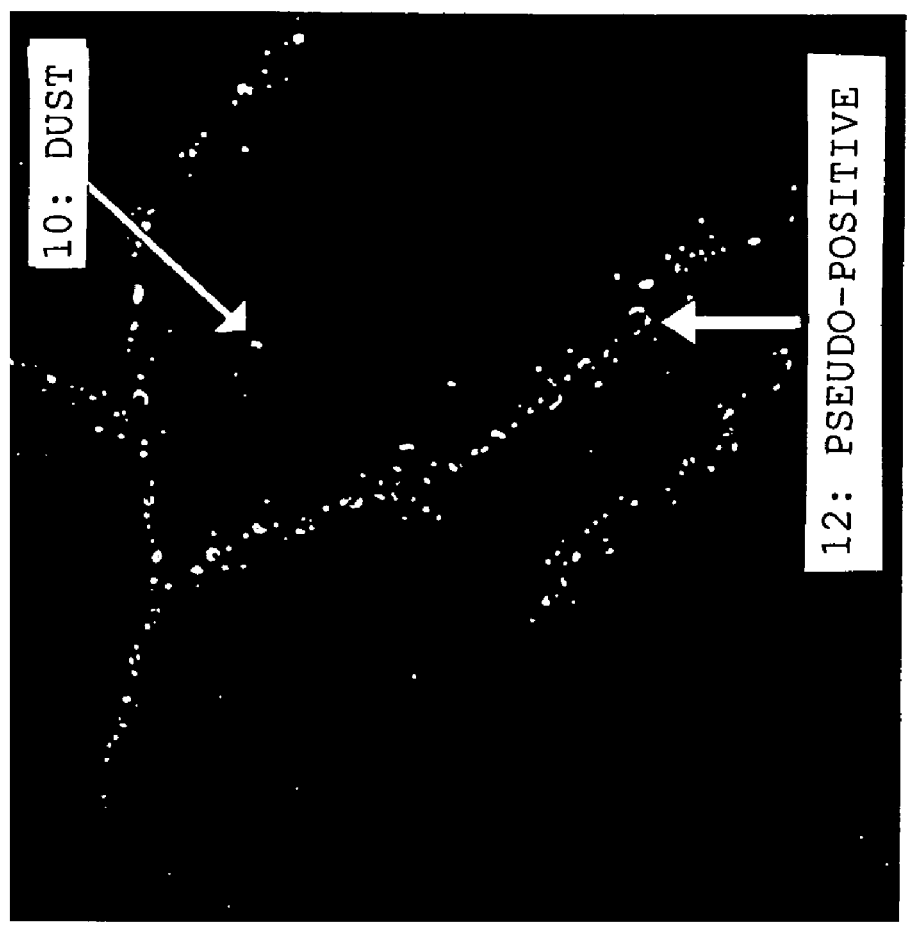
[FIG. 12]

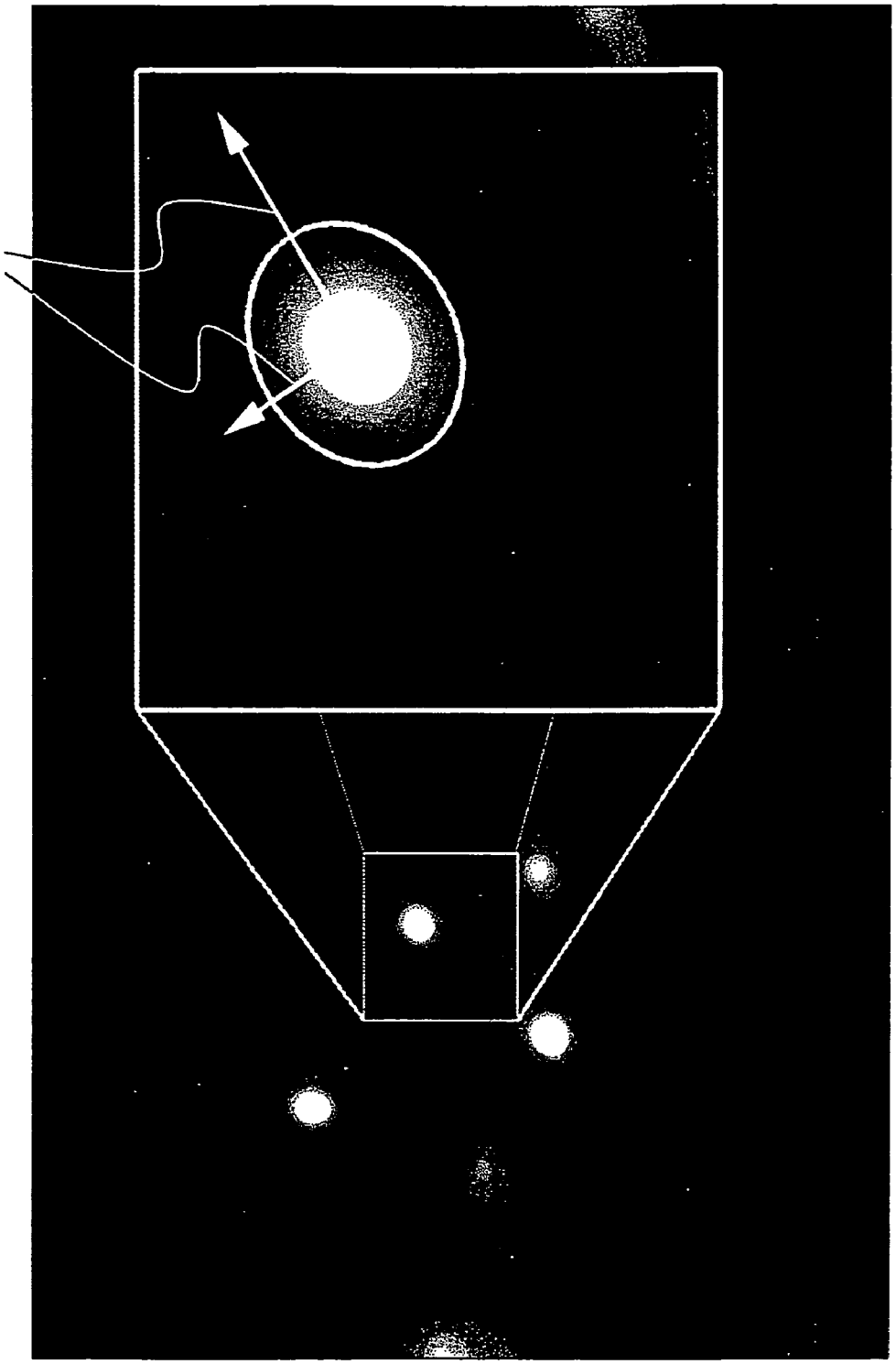

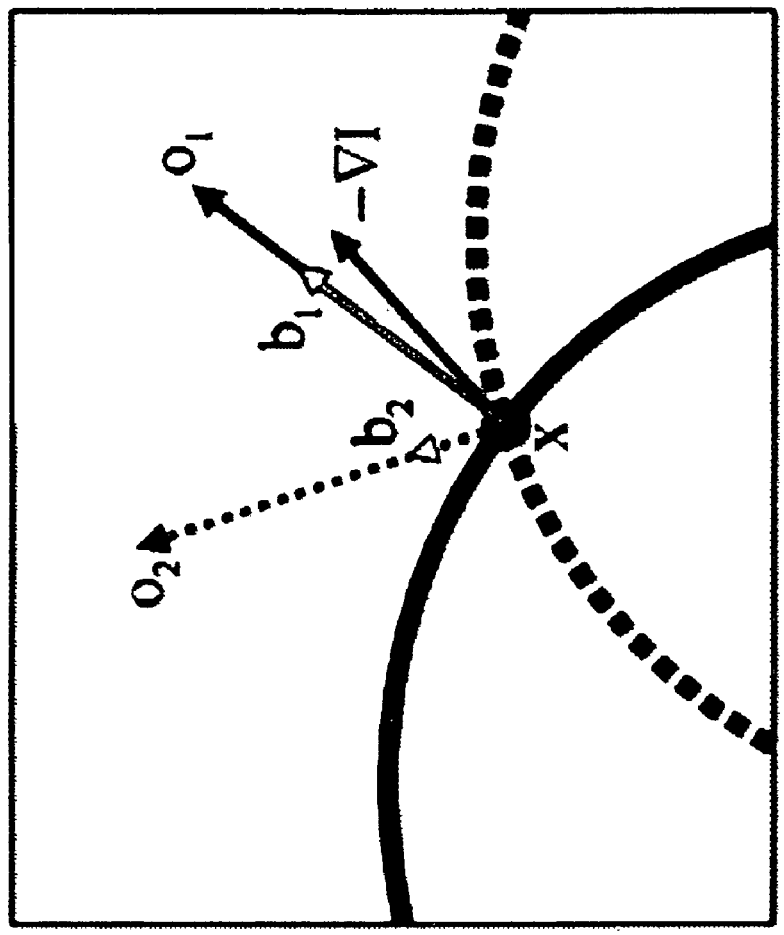
[FIG. 14]

[FIG. 15]
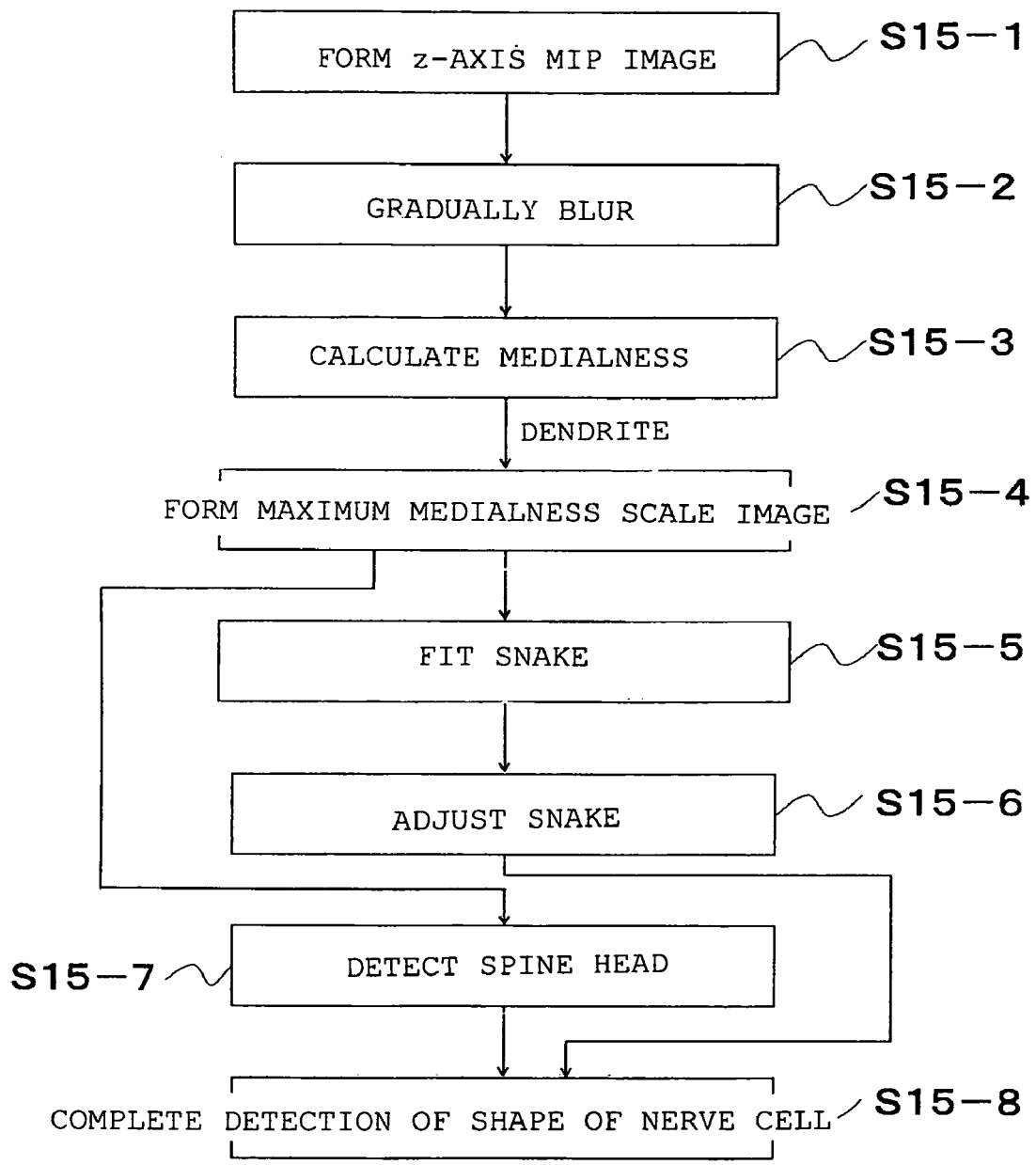

[FIG. 16]
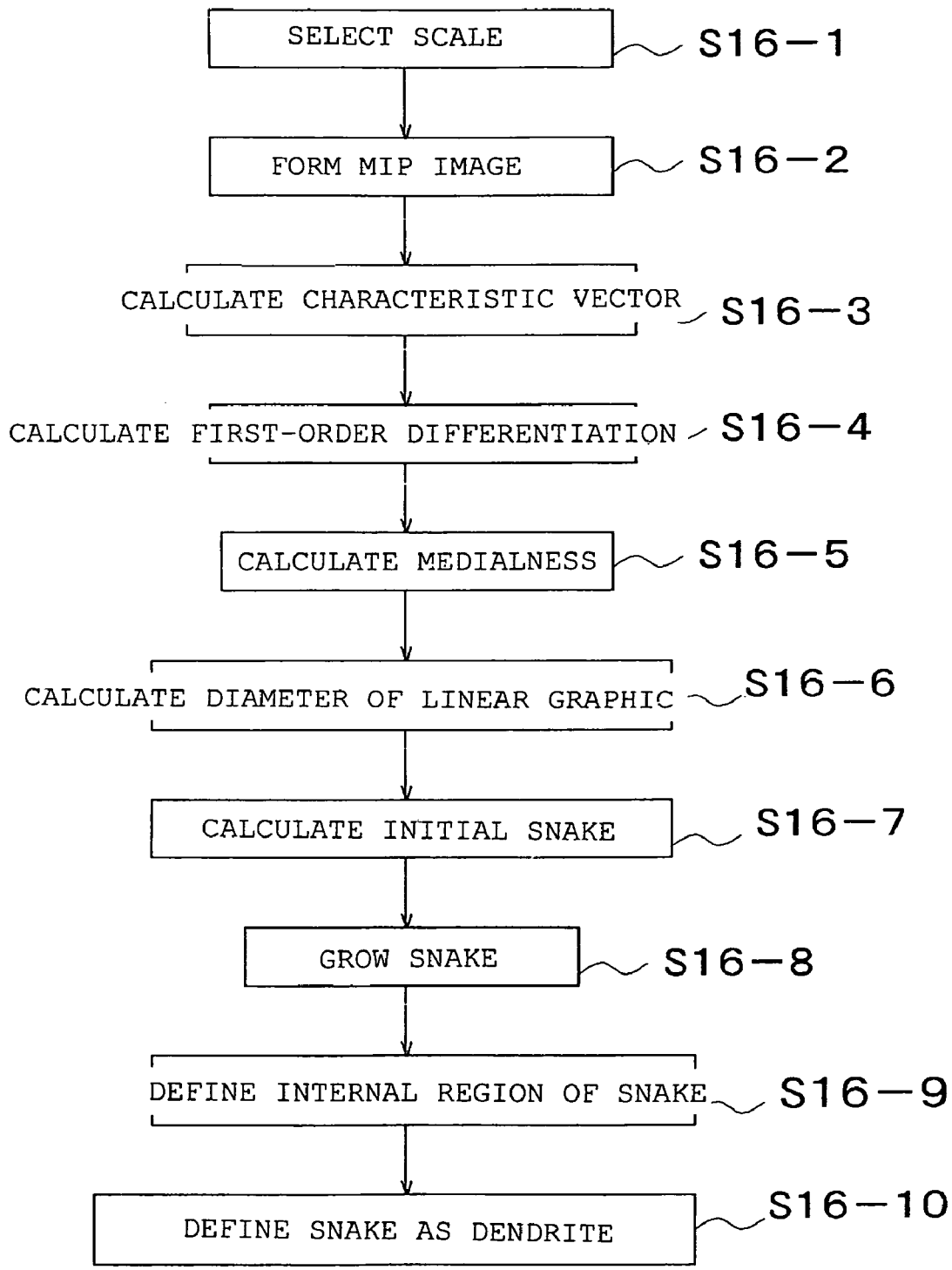

METHOD OF ANALYZING CELL OR THE LIKE HAVING LINEAR SHAPE, METHOD OF ANALYZING NERVE CELL AND APPARATUS AND PROGRAM FOR PERFORMING THESE METHODS

TECHNICAL FIELD

The present invention relates to a method of analyzing a cell having a linear shape, a tissue, and an organ. In particular, the present invention relates to a method of analyzing a nerve cell. More particular, the present invention relates to a method of specifying and analyzing an appearance of branches of a nerve cell dendrite and positions, shapes, and the like of spines.

The present invention also relates to an apparatus which executes these methods and a program which executes the methods.

BACKGROUND ART

Conventionally, a large amount of labor is required to analyze a nerve cell. For example, in visual analysis of a nerve cell based on a microscope image, a method of inputting figure information of a single nerve cell to a computer relying on a manual operation which checks nerve cells with the eyes of a skilled researcher one by one is mainly employed. In such an operation, simple software for visualization is frequently used in visualization. However, the operation includes a large number of operations, and consequently, quantity of work tends to be large.

For example, it is not uncommon that several days are required to complete analysis of one image.

This is because a nerve cell has a complex figure in which one nerve cell includes several tens of dendrites, and each dendrite has several tens of thousands of spines (post-synaptic regions) thereon. For the complex structure, in a conventional image processing algorithm, it is difficult to automatically analyze a figure of a nerve cell.

Examples of Prior Patent Document

For example, in the following Patent Document 1, a method of evaluating a cell body having a linear structure is described. The method described in the Patent Document 1 is a method of obtaining a degree of extension of a neurite or the like from image data. The method is characterized in that the number of cell bodies, an area of the cell bodies, and a length and an area of a linear structure are calculated by image processing.

In the following Patent Document 2, a method of screening a compound specifically influencing growth of a neurite by using reporter molecules having fluorescent dye is described. An optical analyzing system, a chemical, and the like used in the method are also described in the Patent Document 2.

In the following Patent Document 3, a cell screening method is described. In this method, a microscope, a system which converts a microscope image into a digital image, software to classify cell substances, and the like are used.

Patent Document 1: Japanese Patent Application Laid-Open No. 2002-207993
Patent Document 2: Japanese Patent Application Laid-Open No. 2005-95172
Patent Document 3: Japanese Patent Application Laid-Open No. 2005-525550

DISCLOSURE OF THE INVENTION

Problem to be Solved by the Invention

It is apparent from research by the present inventors that the spines increase or decrease in number with activity of a nerve and serve an important role in "memory". Observation and analysis of the spines clarify a memory behavior and contribute to development of treatment methods of various brain diseases, and have important medical implications.

Since one neuron includes several tens of thousands of spines, it requires an extremely excessive amount of labor to manually analyze these spines. In particular, in order to observe and analyze not only the number of spines but also the figures of the spines, a skilled engineer must continue the operation for days.

Therefore, a method of analyzing a nerve cell, in particular, a method of rapidly analyzing the figure of a nerve cell including an increase/decrease in number of spines have been desired.

The invention of the present application has been made in consideration of such societal demands, and has an object to propose a technique for automatically performing figure analysis of a nerve cell based on a three-dimensional image of the nerve cell. The invention also provides a method, an apparatus, and the like for analyzing the figures of cells and the like having linear figures by applying the technique.

Means for Solving the Problem

A. Method (1) In order to solve the problem, according to the present invention, there is provided a method of analyzing an object based on a three-dimensional image of the object to be analyzed serving as a cell, a tissue, or an organ having a linear figure, including: a first blurring step of performing scale-space transformation to the three-dimensional image based on a predetermined first scale σ; a first medialness step of calculating a first medialness for each pixel of the three-dimensional image after the scale-space transformation; and a linear figure fitting step of calculating a graphic approximated to the linear figure of the object based on the first medialness.

With this configuration, the figure of a cell or the like having a linear figure can be analyzed. For example, a nerve cell, a (capillary) blood vessel, or the like can be preferably analyzed.

(2) According to of the present invention, there is provided a method of analyzing a figure of a nerve cell based on a three-dimensional image of the nerve cell, including: a first blurring step of performing scale-space transformation to the three-dimensional image based on a predetermined first scale σ; a first medialness step of calculating a first medialness for each pixel of the three-dimensional image after the scale-space transformation; and a dendrite fitting step of calculating a graphic approximated to a dendrite of the nerve cell based on the first medialness.

With this configuration, the figure of a nerve cell, in particular, the figure of a dendrite can be automatically analyzed.

(3) According to the present invention, in the nerve cell analyzing method described in (2) described above, the first blurring step performs scale-space transformation by changing a value of the first scale σ to generate a plurality of blurred image groups to scales σ.

(4) According to the present invention, in the nerve cell analyzing method described in (3) described above, the first blurring step changes the value of the first scale σ in the range of 0.2 μm to 5.0 μm to perform scale-space transformation and generates a plurality of blurred image groups to the scales σ.

In order to recognize the figure of a dendrite, the value σ preferably falls within the range of 0.2 μm to 5.0 μm.

(5) According to the present invention, in the nerve cell analyzing method described in (2) described above, the first medialness step calculates an abundance of a boundary surface as a medialness.

Since the abundance on the boundary surface is used as the medialness, a surface of an object can be preferably recognized. More specifically, the boundary source mentioned here means a surface of an object (dendrite).

(6) According to the present invention, in the nerve cell analyzing method described in (2) described above, the first medialness step calculates a center line by using a peel-off method.

Also by using a conventional peel-off method, the figure of a dendrite can be similarly calculated though the accuracy is somewhat deteriorated.

(7) According to the present invention, in the nerve cell analyzing method described in (2) described above, the dendrite fitting step fits a snake to a dendrite based on the calculated medialness.

B1. Apparatus (8) According to the present invention, there is provided an apparatus which analyzes an object based on a three-dimensional image of the object to be analyzed serving as a cell, a tissue, or an organ having a linear figure, including: a first blurring unit which performs scale-space transformation to the three-dimensional image based on a predetermined first scale σ; a first medialness unit which calculates a first medialness for each pixel of the three-dimensional image after the scale-space transformation; and a linear figure fitting unit which calculates a graphic approximated to the linear figure of the object based on the first medialness.

C1. Program (9) According to the present invention, there is provided a program which makes a computer operate as an apparatus which analyzes an object based on a three-dimensional image of the object to be analyzed serving as a cell, a tissue, or an organ having a linear figure, the program causing the computer to execute: a first blurring procedure which performs scale-space transformation to the three-dimensional image based on a predetermined first scale σ; a first medialness procedure which calculates a first medialness for each pixel of the three-dimensional image after the scale-space transformation; and a linear figure fitting procedure which calculates a graphic approximated to the linear figure of the object based on the first medialness.

A2. Method

(10) According to the present invention, the method of analyzing a cell, a tissue, or an organ having a linear figure described in (1) described above includes: a second blurring step of performing scale-space transformation to the three-dimensional image based on a predetermined second scale σ; a second medialness step of calculating a product of characteristic values of Hessian tensors as a second medialness for each pixel of the three-dimensional image after the scale-space transformation by the second blurring step; and a thorn-like portion detecting step of detecting a thorn-like portion present on the linear figure based on the second medialness.

The thorn-like portion includes any thorn-like portion. For example, a spine on a nerve cell is a typical example.

(11) According to the present invention, the nerve cell analyzing method described in (2) described above includes: a second blurring step of performing scale-space transformation to the three-dimensional image based on a predetermined second scale σ different from the first scale σ; a second medialness step of calculating a product of characteristic values of Hessian tensors as a second medialness for each pixel of the third-dimensional image after the scale-space transformation by the second blurring step; and a spine head portion detecting step of detecting a center position of a spine head portion of a nerve cell based on the second medialness.

(12) According to the present invention, in the nerve cell analyzing method described in (11) described above, the value of the second scale σ is changed within the range of 0.1 μm to 0.3 μm to perform scale-space transformation, and a plurality of blurred image groups to the scales σ are generated.

(13) According to the present invention, in the nerve cell analyzing method described in (11) described above, the spine head portion detecting step determines a position where an absolute value of the second medialness exhibits a peak as the center position of the spine head portion.

(14) According to the present invention, in the nerve cell analyzing method described in (11) described above, the spine head portion detecting step determines a position within a predetermined distance from the dendrite as the center position of the spine head portion.

(15) According to the present invention, the nerve cell analyzing method described in (11) described above further includes a spine pillar portion detecting step of dropping a perpendicular line from the calculated center position of the spine head portion to the nearest dendrite and calculating the perpendicular line as a pillar portion of the spine.

(16) According to the present invention, in the nerve cell analyzing method described in (11) described above, the spine detecting step calculates a region in which all characteristic values of Hessian tensors are negative as a presence region in which the spine head portion is present.

(17) According to the present invention, in the nerve cell analyzing method described in (16) described above, the spine detecting step approximates the calculated presence region by an ellipsoid to calculate an approximate graphic of the spine head portion.

B2. Apparatus

(18) According to the present invention, the apparatus which analyzes a cell, a tissue, or an organ having a linear figure described in (8) described above, includes: a second blurring unit which performs scale-space transformation to the three-dimensional image based on a predetermined second scale σ; a second medialness unit which calculates a product of characteristic values of Hessian tensors as a second medialness for each pixel of the three-dimensional image after the scale-space transformation by the second blurring unit; and a thorn-like portion detecting unit which detects a thorn-like portion present on the linear figure based on the second medialness.

C2. Program

(19) According to the present invention, the program which makes a computer operates as an apparatus which analyzes a cell, a tissue, or an organ having a linear figure described in (9) described above causes the computer to execute: a second blurring procedure which performs scale-space transformation to the three-dimensional image based on a predetermined second scale σ; a second medialness procedure which calculates a product of characteristic values of Hessian tensors as a second medialness for each pixel of the three-dimensional image after the scale-space transformation by the second blurring procedure; and a thorn-like portion detecting procedure which detects a thorn-like portion present on the linear figure based on the second medialness.

D. Other Examples of Nerve Cell Analyzing Method

(20) According to the present invention, in the nerve cell analyzing method described in (2) described above, the dendrite fitting step includes: a first selecting step of selecting a point having a maximum medialness based on the calculated medialness; a second selecting step of selecting the point having the maximum medialness from points at a predetermined distance from the point having the maximum medialness; a step of connecting the selected two points to each other to configure an initial snake; and a growing step of selecting a point having the maximum medialness from points at a predetermined distance from an end point of the configured initial snake and connecting the point having the maximum medialness to an existing end point to grow the snake.

(21) According to the present invention, in the nerve cell analyzing method described in (20) described above, the point to be selected in the growing step is a point at a predetermined distance from the existing end point.

(22) According to the present invention, the nerve cell analyzing method described in (20) or (21) described above includes: a control step of continuing the growth in the growing step when the point to be selected in the growing step can be detected, and completing the growth in the growing step when the point to be selected cannot be detected.

(23) According to the present invention, in the nerve cell analyzing method described in (22) described above, the case in which the point to be selected in the growing step can be detected is a case in which the point to be selected can be detected from a region in the image except a region already recognized as an inside of a snake.

(24) According to the present invention, the nerve cell analyzing method described in (20), (21), (22), or (23) described above includes a defining step of obtaining a diameter at each node of the grown snake to define a region in the snake.

(25) According to the present invention, the nerve cell analyzing method described in (20), (21), (22), (23), or (24) described above includes a repeat control step of defining the grown snake as a dendrite when the snake satisfies both of two conditions including (a) a condition in which the snake has at least three nodes and (b) a condition in which an average medialness of all nodes is not less than a predetermined rate of an average medialness of predetermined dendrites defined up to now, and, when the snake does not satisfy any one of the conditions, discarding the snake and returning to the first selecting step to restart the operation of selecting a point having the maximum medialness.

Effect of the Invention

As described above, according to the present invention, analysis of a cell or the like having a linear figure can be efficiently performed. In particular, when an object is a nerve cell, an appearance of a dendrite of the nerve cell and a figure of a spine appearing on the dendrite can be efficiently analyzed.

BRIEF DESCRIPTION OF THE DRAWINGS

FIG. 1 is an explanatory diagram of a shape of a nerve cell.
FIG. 2 is an explanatory diagram of three-dimensional image data.
FIG. 3 is an explanatory diagram of figures of various spines.
FIG. 4 is an explanatory diagram of a change in number (change in density) of spines depending on a stress steroid effect.
FIG. 5 is an explanatory diagram for explaining a state of conventional image analysis.
FIG. 6 is a conceptual diagram of three characteristic steps in the embodiment.
FIG. 7 is an explanatory diagram showing a state of noise removal by σ convolution.
FIG. 8 is an image of a medialness.
FIG. 9 is an explanatory diagram showing an example which expresses a dendrite by connecting cylinder graphics.
FIG. 10 is an explanatory diagram of a peel-off method.
FIG. 11 is an explanatory diagram of a product of characteristic values of Hessian tensors.
FIG. 12 is an explanatory diagram showing a state of removing a pseudo-positive candidate in selecting a candidate of a spine head portion.
FIG. 13 is an explanatory diagram of main axes.
FIG. 14 is an explanatory diagram of a gradient vector.
FIG. 15 is a flow chart illustrating an operation in the example.
FIG. 16 is a flow chart illustrating an operation in Example 2.

REFERENCE NUMERALS

10 Dust
12 Pseudo-positive

BEST MODE FOR CARRYING OUT THE INVENTION

Preferred embodiments of the present invention will be described below with reference to the accompanying drawings.

1. Figure of Nerve

FIG. 1 shows an explanatory diagram of a figure of a nerve cell. In this embodiment, as the figure of the nerve cell, image data of the nerve cell is obtained by injecting a fluorescent dye to a target nerve cell and observing the nerve cell by a confocal microscope. The image data is a 1024×1024-dot image, and the size of one dot is 0.043 μm.

By changing a position of a plane observed (photographed) by the confocal microscope in a depth direction (direction perpendicular to the plane), plane image data at different positions changed by 45 μm in the depth direction can be obtained.

This state is shown in FIG. 2. In this embodiment, for example, 30 plane image data at positions changed at 0.45-μm intervals are photographed. Since a group of the 30 1024×1024-dot image data three-dimensionally represents a figure of a nerve cell, the group of the 30 image data is called "three-dimensional image data" in this embodiment.

As shown in FIG. 1, dendrites extend peripherally from a nerve cell to form a complex figure. It is known that projections called spines (may be called spinous processes) are generated on the dendrite.

A diagram showing a figure of spines is shown as (2) in FIG. 1. As shown, it is known that the spines are small projections each having a size of about several microns and that a single nerve has approximately ten thousand spines. A density of spines is about 1 spine/1 μm.

According to a research by the inventors of this application, it was found that the spines serve an important role with respect to memory. Observation of generation of spines is a very important issue in searching for a mechanism of memory. However, about ten thousand spines are present in one nerve cell, and thus manual analysis of a figure of the spines from image data requires very troublesome operation.

In the embodiment, a method of efficiently calculating a figure of a nerve cell will be described below. In particular, a method of efficiently calculating figures of a nerve cell including a figure of a dendrite and a figure of spines will be described below.

2. Figure of Spines

FIG. 3 shows a diagram for explaining figures of various spines. As shown in FIG. 3, as the figures of spines, four types of figures including thin, stubby, mushroom, and filopodium are known.

FIG. 4 is an explanatory diagram of a change in number (change in density) of spines depending on a stress steroid effect. In the graph in the diagram, black denotes a change in density of mushroom spines, diagonal lines denote a change in density of thin spines, white denotes a change in density of filopodium spines, and vertical stripes denote a change in density of stubby spines.

As shown, it is known that the number (density) of spines changes by giving stress.

3. Conventional Spine Analysis

At present, a typical method of examining a figure of a nerve cell is a method of calculating a figure of a nerve cell, in particular, the number of spines or the like from image data of the nerve cell by a manual operation. Typically, image analysis of a nerve cell is performed by using a program named Neurolucida (trade name). A state of the image analysis is shown in FIG. 5. FIG. 5(1) is an original image obtained by a confocal microscope. An operator visually determines a position of a spine and determines the length and width of a pillar portion of the spine. This state is shown in a photograph of FIG. 5(2).

However, it is known that, if the spine is simplified, the spine is roughly configured by a head portion (head) and a pillar portion connecting the head to a dendrite (see FIG. 5(3)).

Desirably, as shown in FIG. 5(3), widths w1 and w2 of the ellipsoid head portion, a length (long side of the ellipsoid) t of the head, a length h of the pillar portion, and an angle θ1 between the pillar portion and the dendrite are preferably calculated for each spine.

In the conventional method, only a length t and a width w (value considered as an average value of w1 and w2) can be determined. Calculation needs to be repeated until parameters (w and t in the conventional technique) of an ellipsoid of the head are obtained, and thus a lot of operation labor of the operator tends to be excessive. Since a proportion of manual operation is high, the method is disadvantageously difficult to cope with enormous quantity of data.

In the embodiment, an example in which w1, w2, t, and h of these parameters are automatically calculated is shown.

4. Basic Algorithm in the Embodiment and Characteristics Thereof

In the embodiment, a plurality (for example, 20 to 30 screens) of images (for example, 1024×1024 dots) photographed with a confocal microscope are prepared to configure three-dimensional image data.

A method of inputting the three-dimensional image data to rapidly obtain a figure of a nerve cell is proposed. The method according to the embodiment includes the following three characteristic steps. A conceptual diagram of the three steps is shown in FIG. 6.

(Step 1)
Dendrite tracing: A dendrite is traced by using a scale space method. In this case, irregularities are reduced by using σ convolution blurring to identify a center line of the dendrite. A conceptual diagram of step 1 is shown as step (1) in FIG. 6.

(Step 2)
Detection of spine position: A negative curvature is searched for by using the Hessian tensor method. Since a portion having a negative curvature is considered to correspond to a spindle-shaped "head", a portion having a negative curvature on all coordinate axes is determined as a "head". A spine position in this step (2) is a position of the "head". A conceptual diagram of step 2 is shown as step (2) in FIG. 6.

(Step 3)
Since a head of a spine is considered to be able to be approximated by an ellipsoid (irregular triaxial ellipsoid), the head is regarded as an ellipsoid to perform approximation. In this manner, a minor axis, an intermediate axis, and a major axis are calculated. Of axes in a main-axis direction, the longest axis is called a major axis (t), the second longest axis is called an intermediate axis (w2), and the shortest axis is called a minor axis (w1). See (3) in FIG. 5.

The pillar portion of the spine is recognized as a perpendicular line dropped from the spine to a dendrite closest to the spine. A conceptual diagram of step 3 is shown as step (3) in FIG. 6.

The dendrite obtained as described above is combined with the spine head and the pillar portion to obtain a final figure of the nerve cell.

An operation of a nerve cell analyzing method according to the embodiment will be described below with a central focus on a principle of operation of the above characteristic steps.

4-1. Step 1: Dendrite Tracing 4-1-1. σ Convolution

In the embodiment, a scale-independent analyzing method is employed by using a scale space. More specifically, a scale σ matched with the size of an object is selected. For example, when a dendrite is to be traced, the scale σ is set within the range of 0.2 μm to 5.0 μm. If the spine is an object, the scale σ is set within the range of 0.1 μm to 0.3 μm. As a result, an uneven structure smaller than the scale σ is blurred by the "σ convolution" to remove noise.

In this step 1, since a dendrite is traced, the scale σ is set to σ=0.2 to 5.0 μm.

An equation of the σ convolution is as follows:

$$I(\sigma blur) = I * K(\sigma) = \int I(x') \exp(-(x-x')^2/2\sigma^2) dx'$$

convolution integral $$K(\sigma) = N \exp(-(x-x')^2/2\sigma^2) \qquad \text{[Numerical Expression 1]}$$

where I is a luminance of each pixel constituting an image, and convolution with K(σ) is calculated to blur the image. An equation of K(σ) is given as the above equation. In this equation, N is a constant for normalization and is a number which is determined such that a result obtained by integrating a kernel function K(σ) in a whole space is 1. For example, in a two-dimensional image, $N = 1/(2\pi\sigma^2)$ is given.

In the numerical expression 1, the process in only the x-axis direction is described. However, the same process is also performed in the y-axis and z-axis directions.

A state of noise removal by the σ convolution is shown in FIG. 7. FIG. 7(1) shows original image data, and FIG. 7(2) shows a result of the σ convolution obtained when σ is set to σ=0.5 μm. FIG. 7(3) shows a result of the σ convolution obtained when σ is set to σ=1.0 μm. FIG. 7(4) shows a result of the σ convolution obtained when σ is set to σ=2.0 μm. In the embodiment, since noise is removed to trace a dendrite of a nerve cell, σ is set within the range of 0.2 μm to 5.0 μm.

Actually, the value σ is changed in steps within the range of 0.2 μm to 0.5 μm to form a blurred image. The value σ is changed as, for example, σ=0.5 μm, σ=0.6 μm, σ=0.7 μm, . . . , to generate blurred images for the respective values σ. In an example described below, a more detailed operation of generating a blurred image group is described.

Two types of blurred image groups are formed. The first blurred image group is to trace the dendrite. The second blurred image group is to detect a spine head.

The second blurred image group to detect the spine head is formed in the same manner as the first blurred image group for a dendrite except that the value σ to be changed falls within the range of 0.1 to 0.3 μm.

4-1-2. Medialness Transform

After noise is removed by the scale-space transformation (σ convolution), medialness transform is performed to trace a dendrite and to detect a spine head.

When a dendrite is to be traced, an abundance on a boundary surface is used as a medialness. On the other hand, when a spine head is to be detected, a product of characteristic values of Hessian tensors is used as a medialness. Trace of the dendrite will be described below. Calculation of the medialness of the spine head will be described in the next section 4-2.

Dendrite Tracing

Hessian tensors of pixels of each image of the blurred image group after the scale-space transformation are calculated, and characteristic vectors of the Hessian tensors are calculated. A first gradient vector of a luminance at a position (pixel) "advanced" by the value σ in directions (both sides) of a vector belonging to the minimum characteristic value (negative value) of the characteristic vectors is calculated. Similarly, a second gradient vector of a luminance at a position (pixel) "retreated" by the value σ is calculated.

An inner product of the first gradient vector and a vector obtained by normalizing the characteristic vector is calculated. A value obtained by multiplying the inner product by −1 is called a "degree of boundary in the first scale σ". Similarly, an inner product between the second gradient vector and the vector obtained by normalizing the characteristic vector is calculated. A value obtained by multiplying the inner product by −1 is called a "degree of boundary in the second scale σ".

A smaller one (positive value) of the "degree of boundary in the first scale σ" and the "degree of boundary in the second scale σ" is defined as a "medialness" in the pixel.

The medialness is a scale representing an abundance on a boundary surface, and the boundary surface refers to a surface of an object, i.e., a dendrite.

When a position where a luminance (value) of the medialness is maximum is traced, a main line (center line) and a width (thickness) of the dendrite can be traced. The width (thickness) is a value of the scale σ which gives a maximum medialness.

An image of the medialness is shown in FIG. 8. FIG. 8(1) shows original image data, and FIG. 8(2) is an image (called a medialness image) of a medialness calculated for each pixel when σ=0.5 μm. Similarly, FIG. 8(2) is a medialness image calculated for each pixel when σ=1.5 μm. Similarly, FIG. 8(3) is a medialness image calculated for each pixel when σ=1.5 μm. FIG. 8(4) is a medialness image calculated for each pixel when σ=2.0 μm.

In this manner, medialness images are respectively calculated for a plurality of blurred image groups.

In these drawings, a pixel having a large medialness (bright image) shows that a cylinder graphic having a radius σ passes through the pixel.

More specifically, in the images in FIGS. 8(2) to FIG. 8(4), a line obtained by tracing the maximum values of brightness is a center line of the dendrite. The images show that the cylinder graphic having the radius σ passes through the pixel around the center line.

The cylinder graphic, in brief, is a graphic model obtained by cutting a circular cone along a predetermined section, and will be described in detail later. In the embodiment, a dendrite is expressed (approximated) by connecting the cylinder graphics. An example in which a dendrite is expressed by actually connecting the cylinder graphics is shown in FIG. 9.

In the embodiment, as an energy function, an energy function consisting of a sum of a medialness and a distortion is defined. By solving the energy minimization problem, the dendrite is fit to an actual dendrite.

Fit (or fitting), in brief, is approximation. More specifically, the fit means that "an ideal basic graphic is caused to correspond to a graphic which actually exists". Fit also means that "a corresponding basic graphic with minimum error is given".

An equation of the energy function in the embodiment is shown as follows:

$$E_{snake} = \begin{array}{c} medialness + \\ distortion: \; energy \; function \end{array} \quad \text{[Numerical Expression 2]}$$

$$\hat{E}_{snake} = \sum_{i=1}^{n} E_{snake}(i)$$

$$= \sum_{i=1}^{n} (\alpha E_{ext}(i) + (1-\alpha) E_{int}(i)).$$

In the embodiment, this energy function is called a snake function.

A snake is a set of nodes (snake cells) including positions, thicknesses, and connection information. Here, the connection information is information representing to which snakecell a certain snakecell is connected. The position and the thickness are called spatial parameters, and the connection information is called a topological parameter. In the embodiment, since the connection information is formed by automatically connecting at most two adjacent snakecells to each other, fitting is performed with respect to only the spatial parameter.

Since the spatial parameter is a complex of a position (three dimension) and a thickness (one dimension), it is appropriate to consider a four-dimensional space. The four-dimensional space is a scale space. Calculation of medialness corresponds to plotting "a degree of presence of a linear graphic" in the four-dimensional space.

In the equation, Eext(i) is obtained by inverting the sign of the medialness in the position and the thickness of an ith snakecell. If the value is small, it means that a line graphic having a specified thickness passes through a position specified by the parameters of the snakecell. Eint(i) represents internal energy of the ith snakecell. This energy is energy to prevent a snake from being excessively curved, and a curvature of the snake at the snakecell is used. If the value is small, it means that the snake is linear at the snakecell. σ is a distribution constant which does not change during the fitting.

Importance is attached to the medialness energy when σ is large, and importance is attached to internal energy when σ is small to perform fitting.

Eext(i), as described above, is an medialness (although the sign is inverted) of the position and the thickness of the ith snakecell. Under a condition of constraint in which the snake is prevented from being excessively curved, a medialness (energy) the sign of which is inverted is minimized to calculate a snake passing through a part with high medialness in the scale space. This is the fitting of the snake. Change parameters in the fitting are spatial parameters (position and thickness of a snakecell).

Modification of Medialness Transform

When a spine on a dendrite is relatively large, the spine remains as a thorn in the medialness transform described above. For this reason, trace may be difficult. Therefore, a center line is also preferably obtained by using a so-called "peel-off method" conventionally used.

An explanatory diagram of the peel-off method is shown in FIG. 10.

The peel-off method is one of methods of calculating a center line of an object, and is a method of removing points (pixels) included in the object to cause the center line to remain. An example to which the peel-off method is applied is shown in FIG. 10. FIG. 10(1) shows original image data. The original image data is binarized, and thereafter, pixels are removed from a periphery portion pixel by pixel. The result is shown in FIG. 10(2).

The peel-off method has the following known drawbacks.

(1) Irregularities of a boundary remain as thorns, and automatic trace may fail.

(2) A peel-off result depends on a scale.

However, in the embodiment, since blurring is performed by σ convolution using a scale space method, good trace is likely to be performed even by using the peel-off method in medialness transform.

In the medialness transform by the peel-off method, for example, a maximum luminance of "255" or the like is assigned to pixels corresponding to the obtained center line, and a minimum value of "0" is assigned to the other pixels. As these values, positive and negative values may be used, and "127" and "−128" may be employed.

4-2. Step 2: Detection of Spine Position 4-2-1. Position of Spine Head

A position where a Hessian tensor diagonalized at a scale σ=0.2 μm indicates a negative characteristic value in a three-dimensional space is calculated to detect a spherical portion and a center thereof. The detection of the spherical portion just means extraction of a candidate of a spine head.

The diagonalization at the scale σ=0.2 μm means that, after blurring transformation is performed at the scale σ=0.2 μm, the calculated Hessian tensor is diagonalized.

An image is a map which associates luminances with points in a space. The Hessian tensor is a second-order differentiation of the luminance distribution and represents a local curvature.

Therefore, a negative curvature in a three-dimensional image corresponds to a spine which spherically rises. In the embodiment, focusing on this, a presence region of spines is detected by using the Hessian tensor.

In general, differentiation of a digital signal is calculated by being replaced with difference. For example, an equinox formula or the like is generally used. In this embodiment, such a conventional method may preferably be employed.

In the embodiment, since blurring transformation which can be written in the form of a convolutional integral is performed, a differential operation to an image results in a differential operation to a convolution kernel. More specifically, the kernel function which is differentiated first is prepared and convolutionally integrated to simultaneously perform blurring transformation and differentiation. As a result, an amount of calculation can be saved, and a figure of a nerve cell can be rapidly calculated.

An equation of a Hessian tensor is as follows.

【数3】

$$H = \begin{pmatrix} \frac{\partial^2 I}{\partial x^2} & \frac{\partial^2 I}{\partial x \partial y} & \frac{\partial^2 I}{\partial x \partial z} \\ \frac{\partial^2 I}{\partial y \partial x} & \frac{\partial^2 I}{\partial y^2} & \frac{\partial^2 I}{\partial y \partial z} \\ \frac{\partial^2 I}{\partial z \partial x} & \frac{\partial^2 I}{\partial z \partial y} & \frac{\partial^2 I}{\partial z^2} \end{pmatrix}$$ [Numerical Expression 3]

This Hessian tensor is diagonalized at a scale σ=0.2 μm to calculate characteristic values. An equation obtained after the diagonalization is described below.

【数4】

$$diag\ H = \begin{pmatrix} \lambda_1 & 0 & 0 \\ 0 & \lambda_2 & 0 \\ 0 & 0 & \lambda_3 \end{pmatrix}$$ [Numerical Expression 4]

From the characteristic values λ1, λ2, and λ3 thus obtained, a curvature of the portion (pixel) is found. In the spherical graphic, since all the characteristic values λ1, λ2, and λ3 are negative, only pixels satisfying the condition are extracted to generate a new image.

More specifically, the absolute value (−λ1·λ2·λ3) of the characteristic values is assigned as pixel value to the pixels in which all the characteristic values are negative as pixel values, and 0 is assigned to the other pixels to generate a new image. This image is a medialness image to detect a spine position.

The pixel having a medialness of 0 means that the position of the pixel is not in the spine region, and the pixel having a medialness of non-0 means that the position of the pixel is in a region in which a spine is present.

A characteristic feature in the embodiment is that a product of characteristic values of Hessian tensors is used as a medialness to detect a spine position (detect a region in which a spine is present and detect a center position of a spine head).

In this manner, by calculating a position (pixel) representing a negative characteristic value in a three-dimensional image, a spherical portion corresponding to the spine head (region in which the spine head is present) can be calculated. Furthermore, the center position of the spine head can be detected from the peak position of the absolute value of the product of the characteristic values.

A characteristic feature in the embodiment is "medialness transform" used in detection of a spine head, and in particular, a significant feature is that a product of characteristic values of Hessian tensors is used as a "medialness".

The "center portion" of the spine head, as described above, is a point (pixel) which gives a peak value, i.e., a maximum value of the absolute value of the product λ1·λ2·λ3 of characteristic values. This is shown in FIG. 11. FIG. 11(1) shows original image data, and FIG. 11(2) shows image data representing the value of the product λ1·λ2·λ3 of the characteristic values. In FIG. 11(2), a position which exhibits a maximal value of the product $\lambda 1 \cdot \lambda 2 \cdot \lambda 3$ of the characteristic values is indicated by an arrow.

A spherical portion (pixel in which all characteristic values are negative) obtained as described above serves as a candidate of the spine head. This is because a negative curvature in a three-dimensional image is considered to be derived from the spherical spine head.

In the embodiment, when a candidate is to be selected, a range to which a calculation is applied is limited to a periphery of a dendrite fitted in advance. By this limitation, a pseudo-positive candidate 12 is removed. This is shown in FIG. 12. As shown in FIG. 12, in the embodiment, a candidate center position (the point (pixel) which gives the peak value) which is 8 μm or more distant from a dendrite is regarded as a dust 10 and excluded from the candidates of the spine head.

A characteristic vector of a Hessian tensor indicates a main axis when the spherical portion is regarded as an ellipsoid.

4-2-2. Detailed Detection of Spine Head and Pillar Portion

In order to analyze a figure of a spine in detail, a head is approximated by an ellipsoid, and parameters of the size of the head are obtained. With respect to the spine head, a most appropriate ellipsoid is obtained from the direction of the main axis and the analysis of inertia moment around the axes. The main axis is a direction of a characteristic vector at a luminance center of the detected spine head.

By the parameters of the ellipsoid obtained as described above, w1, w2, and t are calculated as described in FIG. 5.

The "main axis" is a "main axis of quadric surface". Intuitively, the "main axis" is an orthogonal axis indicating a most characteristic direction of a graphic". For example, in a graphic like a rugby ball, the longest direction and two directions constituting a plane orthogonal to the longest direction are main axes (a total of 3 axes).

While a two-dimensional graphic has two main axes, a three-dimensional graphic (in the case of an actual spine) has three main axes. An ellipsoid is also a kind of a quadric surface.

An explanatory diagram of main axes is shown in FIG. 13. In this diagram, one arrow indicates a major axis, and the other indicates a minor axis. Since FIG. 13 shows a plane, for descriptive convenience, only two main axes are shown. However, an actual spine includes three main axes. A basis which diagonalizes a Hessian tensor corresponds to the main axes.

A method of examining a position of a boundary surface which is present in the direction of the main axis and performs fitting by an ellipsoid under the condition is also preferably used. The boundary surface refers to a surface of an object. In this case, the boundary surface refers to a surface of a spine head.

The examination of the position of the boundary surface is that, in order to estimate a position of a boundary surface being present in an original graphic, an inner product of a first-order differentiation of an image (resulting from the original graphic deteriorated by optical blurring or the like) and an arbitrary directional vector o is calculated, and a place where the inner product is large is defined as a "place where a boundary surface orthogonal to o is present".

The explanatory diagram of this is shown in FIG. 14. In FIG. 14, a first-order differentiation $-\Delta I$ of an image and directional vectors (o1, o2) are shown. FIG. 14 also shows the size of an inner product (b1, b2) for both vectors. In FIG. 14, since b1 is larger than b2, it is found that a boundary indicated by a solid line is present.

In this patent, the ellipsoid includes not only a spheroid but also an irregular triaxial ellipsoid (see FIG. 5).

A root of a spine, i.e., a portion where a pillar portion is connected to a dendrite is not easily identified because fluorescence is weak. Therefore, in the embodiment, as described above, the shortest distance between the spine head (center position) and the dendrite is calculated, and this is regarded as the pillar portion of the spine. The shortest distance thus obtained is a length of the pillar portion, i.e., h (see FIG. 5).

4-3.

The spine head, the pillar portion of the spine, and the dendrite obtained as described above are combined with each other to obtain a final figure of a nerve cell.

According to the embodiment, since the figure of the nerve cell can be obtained as a shape also including a spine, the invention can considerably contribute to promotion of the efficiency of research on nervous activity, diagnosis of diseases, and the like.

EXAMPLE 1

5. Example 1

Nerve Cell Figure Automatic High-Speed Analyzing Program

The inventors of the present application implemented the operations described above by a program on a computer to actually examine the processing ability of the operations.

As an object to be processed, a slice of one hippocampus appropriately subjected to drug stimulation was used. This slice was photographed by using a confocal microscope. In this case, a fluorescent dye was injected into the slice in advance.

The photographing resolution was 1024×1024 dots, the number of bits per pixel was 8, and image data in which 256-grayscale luminances were recorded was obtained. An interval between pixels (size of pixel) was 0.043 μm. The image data were photographed 30 times by changing the position at 0.45-μm intervals in a depth direction (z direction) (see FIG. 2).

In this manner, image data of 30 photographs of the 1024× 1024-dots (8 bits/pixel) were obtained in the depth direction. A group of these images is "three-dimensional image data".

The three-dimensional image data (image data of 30 photographs) was supplied to the computer, and the program written by the inventors of the present application in the embodiment was applied to the three-dimensional data to cause the computer to output a figure of a nerve.

A flow chart illustrating an operation of the computer (operation of the program) in the example is shown in FIG. 15.

5-1. Formation of Z-Axis MIP Image

First, as shown in step S15-1 in FIG. 15, a z-axis MIP image is formed based on the input three-dimensional image data. Here, the z-axis MIP image is a two-dimensional image obtained by projecting a given tomographic image in a z-axis direction, in which luminances of respective points are maximum luminances of pixels aligned on a projection line. MIP is an abbreviation of Max Intensity Projection.

A conceptual diagram of the z-axis MIP image is shown in FIG. 16. As shown in FIG. 16, pixels at the same position in the image data of the 30 photographs are extracted (i.e., 30 pixels of the 30 photographs). A value having the highest luminance is extracted from the pixels. The value is assigned to a pixel at a corresponding position in the z-axis MIP image. More specifically, the z-axis MIP image is an image which is newly formed by extracting the value of the maximum luminance from a plurality of images aligned on the z axis.

In the example, in order to reduce an amount of calculation by the computer, three-dimensional image data is projected as two-dimensional image data to form a z-axis MIP image. However, in principle, the three-dimensional image data may preferably be processed without any change as a matter of course.

5-2. Gradual Blurring of Z-Axis MIP Image (Scale-Space Transformation)

As shown in step S15-2 in FIG. 15, images obtained by gradually blurring a z-axis MIP image are formed. More specifically, the scale-space transformation is applied to the z-axis MIP image. In this case, a value σ is gradually changed to form a group of a plurality of gradually blurred images. For example, gradual scales σ such as σ=0.2 μm, σ=0.3 μm, . . . , are used to form a group of a plurality of images.

For example, the value σ is changed in 0.1-μm steps from 0.2 μm to 5.0 μm to form an image group of a total of 49 steps. The image group of the plurality of steps are called "a step blurred image group".

5-3. Calculation of Medialness for Images of Respective Scales

Next, as shown in step S15-3 in FIG. 15, a medialness is calculated based on the step blurred image group.

In order to extract a dendrite, an abundance on a boundary line is used as a medialness. The medialness is calculated for each pixel. An image in which the medialness is assigned to each pixel is formed. This image is called a "medialness image".

The calculation is performed for each image of the plurality of images in the step blurred image group to form a plurality of "medialness images".

In the embodiment, although a differential operation are frequently performed, the differentiation is generally calculated by being replaced with a difference. An equinox formula or the like is generally used. In this example, such a conventional technique may preferably be used as a matter of course.

In the example, however, since blurring transformation which can be written in the form of σ convolutional integral is performed, a differential operation to an image results in a differential operation to σ convolution kernel. More specifically, the kernel function which is differentiated first is prepared and convolutionally integrated to simultaneously perform blurring transformation and differentiation.

As a result, according to the example, an amount of calculation by the computer can be reduced, and an analyzing rate can be improved.

5-4. Maximum Medialness Scale Projection to Medialness Image in σ-Axis Direction As shown in step S15-4 in FIG. 15, a value of the maximum luminance in a σ-axis direction is found for the medialness image. In this case, the maximum luminance refers to the maximum value of the medialness. A value of a scale σ which gives the maximum luminance is extracted, and a "maximum medialness scale image" in which the value of σ is assigned to a corresponding pixel is obtained.

As described above, medialness images are respectively calculated for a group of a plurality of step blurred image group (for example, 20 images) in which the value of σ is changed. Therefore, since a group of a plurality of (for example, 20) medialness images are obtained, pixels which are located at the same positions and have the maximum luminances (maximum medialness) are calculated from the group of images, and a new image in which a scale σ which gives the maximum luminance is assigned to a pixel is formed.

This image is an image in which a position of a pixel having the maximum luminance (maximum medialness) on the a axis (i.e., the value of σ) is assigned. The image is called a "maximum medialness scale image".

Therefore, respective values of the points of the formed projection image (maximum medialness scale image) are given by σ=0.3 μm, σ=0.5 μm, . . . , and the values indicate positions of the scale σ having the largest medialness.

5-5. Moving Snake Search for Position Having Minimal Energy

As shown in step S15-5 in FIG. 15, a snake is moved in the maximum medialness scale image thus obtained to search for a position having a minimal energy.

In this case, a snake is handled as a linear graphic obtained by connecting a plurality of cylinder graphics and having an uneven thickness. In this case, the cylinder graphic is a truncated circular cone. More specifically, a graphic obtained by cutting any circular cone along a plane and removing a portion including the apex is called a cylinder graphic. In this manner, the snake is conveniently handled as graphic configured by cylinder graphics.

A cleft line of a luminance being present in the maximum medialness scale image is detected. In this manner, of the spatial parameters of the snake, fitting of an xy component and fitting of a thickness are completed.

5-6. Adjustment of Snake

As shown in step S15-6 in FIG. 15, the completed snake is returned to an original three-dimensional tomographic image, and fitting of a z-axis component and correction of the thickness are performed.

5-7. Detection of Spine Head

The spine is configured as described above and appropriately adjusted to detect a figure of a dendrite. Since a "dendritic" portion of the dendrite is obtained from the maximum medialness scale image in the above 5-4, an image obtained by removing the dendritic portion from the original image should include a spine. Therefore, from the image of the remaining portion, as shown in step S15-7 in FIG. 15, a spine head is detected.

After the process in the above 5-4 (step S15-4 in FIG. 15), a product of characteristic values of Hessian tensors is calculated to extract a peak position. The peak position is defined as (center position of) a spine head.

As described above, the process is performed to a region except for the "dendritic" portion.

An ellipsoid which includes the center position and in which an error in relation to the spine head is minimized is configured (i.e., approximated), and the ellipsoid is recognized as a spine head.

A perpendicular line is dropped from the center position of the spine head to the dendrite to configure a pillar portion of the spine. A length of the perpendicular line (pillar portion) is examined to know a length (h) of the pillar portion.

The spine head (and the pillar portion) thus obtained is combined to the dendrite (i.e., the snake) extracted in advance to complete the detection of a figure of a nerve cell (step S15-8).

In the example, since the figure of the nerve cell is detected as described above, the shape of the nerve cell including the shape of a spine can be efficiently observed.

5-8. Modification

In the example, a three-dimensional image is projected as a two-dimensional image in the course of the process. However, this projection is performed to reduce processing time of a computer. Theoretically, the three-dimensional image may preferably be processed without any change as a matter of course. In this case, for example, the medialness image is a four-dimensional (depth, width, height, and scale) image.

EXAMPLE 2

6. Example 2

Improved Nerve Cell Analyzing Method 6-1. Background

In the Example 1, a snake (function) is used (Numerical Expression 2) in tracing a dendrite (4-1-2). However, a calculation amount tends to be excessive, and long-term calculation may be performed. In particular, if a plurality of minute structures are present, a huge amount of time may be required to accurately calculate all these structures. As described in the above 5-5, the operation which moves a snake to search for a position having the minimum energy tends to require a very large calculation amount. As a result, it is supposed that diagnosis may be disturbed.

An improved method to more rapidly perform calculation such as tracing a dendrite is proposed as the Example 2 in the description below.

6-2. Principle

The method to be proposed in Example 2 is a method in which a scale-space method and a facet model are combined to detect a linear graphic from an image. The facet model is a framework to study a microstructure having a size smaller than that of a pixel, and is characterized in that insides of pixels are approximated by a polynomial expression and an image is captured as a set of the approximated values.

A two-dimensional image can be represented as a real valued function:

$$f:R^2 \to R \quad \text{[Numerical Expression 5]}$$

When an image f is sufficiently smooth, the following equation is true in the proximity of any point in a domain (Taylor's theorem).

$$f(x+\epsilon u) = \begin{matrix} f(x) + \epsilon df_x(u) + \\ \frac{1}{2}\epsilon^2 d^2 f_x(u) + \ldots \end{matrix} \quad \text{[Numerical Expression 6]}$$

In this equation, when sampling is performed at sufficient accuracy, i.e., when the size of a pixel is sufficiently smaller than the size of the developable proximity, the inside of each pixel can be approximated by the following polynomial expression:

$$f(x+\epsilon u) = \begin{matrix} f(x) + \epsilon \mathrm{grad} f \cdot \\ u + \frac{1}{2}\epsilon^2 u^t H u \end{matrix} \quad \text{[Numerical Expression 7]}$$

However, in order to assist intuitive comprehension, a first-order differentiation and a second-order differentiation are expressed by standard bases, and the standard bases are represented by grad f and H, respectively. In this case, furthermore, when a diagonalization basis of a second-order differentiation tensor (Hessian tensor) is calculated and expressed, the equation (Numerical Expression 7) is further simplified and can be expressed as:

$$f(x+\epsilon u) = \begin{matrix} f(x) + \epsilon(g_+ u_+ + g_- u_-) + \\ \frac{1}{2}\epsilon^2(\lambda_+ u_+^2 + \lambda_- u_-^2) \end{matrix} \quad \text{[Numerical Expression 8]}$$

In this equation, $$\lambda_+, \lambda_- \quad \text{[Numerical Expression 9]}$$

express a larger one and a smaller one of two characteristic values of the Hessian tensors, respectively, and $$g_+, g_- \quad \text{[Numerical Expression 10]}$$

express differential coefficients in corresponding directions. When a linear graphic passes through a pixel in question, one of the characteristic values of the Hessian tensors exhibits a large negative value, and the other exhibits a value close to 0, based on a scale which can sufficiently capture the size of the graphic. In this case, a characteristic vector belonging to the small characteristic value (negative characteristic value) indicates a normal direction of the linear graphic, and is called a main axis in the normal direction. In contrast, since a characteristic vector belonging to the large characteristic value indicates a tangential direction, the characteristic vector is called a main axis in the tangential direction. If the pixel is on the center line of the graphic, the position should have a ridge-like shape, and an extreme value must be set in the normal direction. More specifically, on a straight line expressed by:

$$u_+ = 0 \quad \text{[Numerical Expression 11]}$$

$$\partial_u f(x+\epsilon u)=0 \quad \text{[Numerical Expression 12]}$$

is solved to obtain a position of the extreme value:

$$\epsilon u_- = -\frac{g_-}{\lambda_-} \quad \text{[Numerical Expression 13]}$$

However, this displacement $$\epsilon u_- \quad \text{[Numerical Expression 14]}$$

must be present in the pixel in question. Therefore, the displacement is calculated for all the points in the domain. By checking whether the displacements are included in the pixel, it can be determined whether the points can be present on the center line.

6.3 Process Flow

A flow of concrete processes will be described below with reference a flow chart. FIG. 16 shows a flow chart illustrating the operations according to Example 2. The process flow is a process for tracing a dendrite, and the processes are an alternative to the processes described in the 4-1-2. "Dendrite Tracing" described above. More specifically, the processes can be considered as a modification of the processes from 5-1. to 5-5.

First, in step S16-1, an optimum scale is selected. A scale selecting method will be described in detail later.

In step S16-2, an MIP (Max Intensity Projection) image is formed.

In step S16-3, a smaller characteristic value and a characteristic vector corresponding to the characteristic value are calculated for each pixel of the MIP image. More specifically, $$\lambda_- \quad \text{[Numerical Expression 15]}$$

and the normal direction are calculated.

In step S16-4, a first-order differentiation is calculated for each pixel of the MIP image. More specifically, $$g\_\_$$ [Numerical Expression 16]

is calculated.

In step S16-5, a medialness is calculated for each pixel of the MIP image. In this case, the medialness is a quantity which is given by:

$$|\lambda\_|$$ [Numerical Expression 17]

when the extreme value described in [Example 1] is present in the pixel and which is 0 when the extreme value is not present.

In step S16-6, at a point where the medialness is not zero, a diameter of a linear graphic passing through the point is calculated. The diameter can be calculated by the following sub-processes.

(step a) A point in question is defined as O, and two points obtained by advancing from the point O to both the sides in the normal direction by equal distances are defined as A and B, respectively.

(step b) At the points A and B, degrees of boundary to vectors given by:

$$\vec{OA}/\|\vec{OA}\|, \vec{OB}/\|\vec{OB}\|$$ [Numerical Expression 18]

are respectively calculated. In this case, a degree of boundary β to a vector e is a quantity defined by β=−e·grad f where a differential coefficient at this point is grad f.

(step c) A product of the calculated two degrees of boundary is calculated. This product is expressed by:

$$\tau$$ [Numerical Expression 19]

(step d) Distances from the point O to the points A and B are changed within the range of 0.1 μm to 5.0 μm, and a product of the degrees of boundary at each of the distances:

$$\tau(r)$$ [Numerical Expression 20]

is calculated.

(step e) Of peaks of the products of the degrees of boundary given by:

$$\tau(r)$$ [Numerical Expression 21]

a position which is closest to the center O is defined as an end point of a diameter. In this case, the diameter is obtained as a value which is twice a distance from the end point to the point O.

In step S16-7, an image of the medialness obtained in the step S16-5 is scanned to select a point having the maximum medialness. Furthermore, a point having the maximum medialness is selected from points 1 μm distant from the point. The two selected points are connected by a straight line to obtain a first snake. This snake is called an initial snake.

In step S16-8, new end points are sequentially additionally connected to both the ends of the (initial) snake to grow the snake. However, the new end points are selected under the following conditions.

(condition a) A distance from the original end point to the new end point is 1 μm.

(condition b) The straight line connecting the original end point to the new end point has an angle within ±30° with respect to the unextended straight line.

(condition c) A point having the maximum medialness in points which satisfy the (condition a) and (condition b) is defined as a new end point. The new end point is added to the snake.

(condition d) When (the end points of) the snake reach the boundary of the image and an exclusion region as a result of additional end points to the snake, search for a new end point is stopped. When a new point in the image cannot be found, the search is stopped. When the search is stopped at both the ends of snake, the search for a new end point is ended, growth of the snake is completed, and a final snake is formed.

The end points found as described above finally serve as nodes (nodal points) of the snake, and the end points found at the last serve as end points of both the ends of the snake.

In step S16-9, a diameter is obtained at each of the points (nodes or nodal points) of the formed snake to define a region inside the snake. The internal region is added to the exclusion region of the image.

In step S16-10, when the formed snake includes three or more nodes, and when an average medialness of all the nodes is 10% or more of the medialnesses of the dendrites defined up to now, the obtained snake is defined as a dendrite.

On the other hand, if the condition is not satisfied, the formed snake is discarded and the process returns to step S16-7. This operation is repeated until no snake can be extracted from the image, or is repeated the initially determined number of times, and then ended.

The dendrite is traced as described above.

Selection of Scale

As described above, a method of selecting a scale in step S16-1 will be described below in detail. An operator can freely select a value in a scale range of σ=0.1 μm to 3.0 μm. Processes in steps S16-2 to S16-6 are performed to the value selected by the operator.

An image obtained by plotting a height (not position) of a peak of the products of degrees of boundary obtained in (step e) in step S16-6 on each point is displayed for the operator.

When the operator sees the image and determines that the obtained image appropriately expresses a center line, the processes subsequent to step S16-7 are performed. When it is determined that the image does not express the center line, the process shifts to step S16-1 to reselect another scale.

According to Example 2, a process of sequentially adding end points of the snake to grow the snake is performed in place of fitting of a snake. For this reason, a calculation amount can be reduced, and the method contributes to rapid diagnosis.

7. Other Modifications/Applications (1) In the above embodiment, the method of analyzing a nerve cell is described. However, this method can be directly used in other cells, tissues, and organs having a linear figure or a dendrite figure as a nerve cell.

For example, the method according to the embodiment can also be applied to a tissue formed in a net-like shape such as capillary blood vessels.

In particular, according to the method of the embodiment, even though a thorn-like portion is generated on a linear figure, the thorn-like portion can be efficiently analyzed. A spine is a typical example of the thorn-like portion.

(2) In the embodiment, a three-dimensional image of a cell figure is used as an input. Such a three-dimensional image can easily be photographed using a confocal microscope but may also be obtained by another method or apparatus. For example, other various imaging apparatuses such as a two-photon microscope can be used.

(3) In the above example, a program is installed in a computer, and three-dimensional image data of a nerve cell is analyzed by the computer. However, the program is preferably installed in a hard disk or the like of the computer in advance. The program may preferably be recorded on a CD- ROM or the like in advance and supplied to a desired computer. The program may also preferably be installed in the computer through a network.

The three-dimensional image data to be input is preferably realized by a method in which a plurality of images of a general two-dimensional image format are used and supplied to the computer. As a matter of course, a data format dedicated to specific three-dimensional image data may preferably be formed as appropriate.

The three-dimensional data is preferably once stored in a CD-ROM, various magnetic disks, various optical disks, or various semiconductor storage devices and then supplied to the computer. A configuration in which a microscope and the computer are connected to each other through communication lines to transfer the three-dimensional image data is also preferably employed.

(4) In the embodiment, the nerve cell analyzing apparatus is realized by using a general-purpose computer. However, the nerve cell analyzing apparatus may also preferably be structured by using dedicated hardware.

In particular, when the nerve cell analyzing apparatus and the microscope configure an integral structure, or when the nerve cell analyzing structure is incorporated in an inspection apparatus, the configuration of the dedicated device may be more convenient than a configuration in which a program is installed in a general-purpose computer.

The invention claimed is:

1. A method of analyzing an object based on a three-dimensional image of the object to be analyzed serving as a cell, a tissue, or an organ having a linear figure, comprising:
   a first blurring step of performing scale-space transformation to the three-dimensional image based on a predetermined first scale $\sigma$;
   a first medialness step of calculating a first medialness for each pixel of the three-dimensional image after the scale-space transformation; and
   a linear figure fitting step of calculating a graphic approximated to the linear figure of the object based on the first medialness.

2. The method of analyzing a cell, a tissue, or an organ having a linear figure according to claim 1, comprising:
   a second blurring step of performing scale-space transformation to the three-dimensional image based on a predetermined second scale $\sigma$;
   a second medialness step of calculating a product of characteristic values of Hessian tensors as a second medialness for each pixel of the three-dimensional image after the scale-space transformation by the second blurring step; and
   a thorn-like portion detecting step of detecting a thorn-like portion present on the linear figure based on the second medialness.

3. The program which makes a computer operate as an apparatus which analyzes a cell, a tissue, or an organ having a linear figure according to claim 2, causing the computer to execute:
   a second blurring procedure which performs scale-space transformation to the three-dimensional image based on a predetermined second scale $\sigma$;
   a second medialness procedure which calculates a product of characteristic values of Hessian tensors as a second medialness for each pixel of the three-dimensional image after the scale-space transformation by the second blurring procedure; and
   a thorn-like portion detecting procedure which detects a thorn-like portion present on the linear figure based on the second medialness.

4. A method of analyzing a figure of a nerve cell based on a three-dimensional image of the nerve cell, comprising:
   a first blurring step of performing scale-space transformation to the three-dimensional image based on a predetermined first scale $\sigma$;
   a first medialness step of calculating a first medialness for each pixel of the three-dimensional image after the scale-space transformation; and
   a dendrite fitting step of calculating a graphic approximated to a dendrite of the nerve cell based on the first medialness.

5. The nerve cell analyzing method according to claim 4, wherein
   the first blurring step performs scale-space transformation by changing a value of the first scale $\sigma$ to generate a plurality of blurred image groups to scales $\sigma$.

6. The nerve cell analyzing method according to claim 5, wherein
   the first blurring step changes the value of the first scale $\sigma$ in the range of 0.2 μm to 5.0 μm to perform scale-space transformation and generates a plurality of blurred image groups to the scales $\sigma$.

7. The nerve cell analyzing method according to claim 4, wherein
   the first medialness step calculates an abundance of a boundary surface as a medialness.

8. The nerve cell analyzing method according to claim 4, wherein
   the first medialness step calculates a center line by using a peel-off method.

9. The nerve cell analyzing method according to claim 4, wherein
   the dendrite fitting step fits a snake to a dendrite based on the calculated medialness.

10. The nerve cell analyzing method according to claim 4, comprising:
    a second blurring step of performing scale-space transformation to the three-dimensional image based on a predetermined second scale $\sigma$ different from the first scale $\sigma$;
    a second medialness step of calculating a product of characteristic values of Hessian tensors as a second medialness for each pixel of the third-dimensional image after the scale-space transformation by the second blurring step; and
    a spine head portion detecting step of detecting a center position of a spine head portion of a nerve cell based on the second medialness.

11. The nerve cell analyzing method according to claim 10, wherein
    the value of the second scale $\sigma$ is changed within the range of 0.1 μm to 0.3 μm to perform scale-space transformation, and a plurality of blurred image groups to the scales $\sigma$ are generated.

12. The nerve cell analyzing method according to claim 10, wherein
    the spine head portion detecting step determines a position where an absolute value of the second medialness exhibits a peak as the center position of the spine head portion.

13. The nerve cell analyzing method according to claim 10, wherein
    the spine head portion detecting step determines a position within a predetermined distance from the dendrite as the center position of the spine head portion.

14. The nerve cell analyzing method according to claim 10, comprising a spine pillar portion detecting step of dropping a perpendicular line from the calculated center position of the spine head portion to the nearest dendrite and calculating the perpendicular line as a pillar portion of the spine.

15. The nerve cell analyzing method according to claim 10, wherein the spine detecting step calculates a region in which all characteristic values of Hessian tensors are negative as a presence region in which the spine head portion is present.

16. The nerve cell analyzing method according to claim 15, wherein the spine detecting step approximates the calculated presence region by an ellipsoid to calculate an approximate graphic of the spine head portion.

17. The nerve cell analyzing method according to claim 4, wherein the dendrite fitting step includes:

a first selecting step of selecting a point having a maximum medialness based on the calculated medialness;

a second selecting step of selecting the point having the maximum medialness from points at a predetermined distance from the point having the maximum medialness;

a step of connecting the selected two points to each other to configure an initial snake; and a growing step of selecting a point having the maximum medialness from points at a predetermined distance from an end point of the configured initial snake and connecting the point having the maximum medialness to an existing end point to grow the snake.

18. The nerve cell analyzing method according to claim 17, wherein the point to be selected in the growing step is a point at a predetermined distance from the existing end point.

19. The nerve cell analyzing method according to claim 17, comprising:

a control step of continuing the growth in the growing step when the point to be selected in the growing step can be detected, and completing the growth in the growing step when the point to be selected cannot be detected.

20. The nerve cell analyzing method according to claim 19, wherein the case in which the point to be selected in the growing step can be detected is a case in which the point to be selected can be detected from a region in the image except a region already recognized as an inside of a snake.

21. The nerve cell analyzing method according to claim 17, comprising:

a defining step of obtaining a diameter at each node of the grown snake to define a region in the snake.

22. The nerve cell analyzing method according to claim 17, comprising:

a repeat control step of defining the grown snake as a dendrite when the snake satisfies both of two conditions including:

(1) a condition in which the snake has at least three nodes; and (2) a condition in which an average medialness of all nodes is not less than a predetermined rate of an average medialness of predetermined dendrites defined up to now, and, when the snake does not satisfy any one of the conditions, discarding the snake and returning to the first selecting step to restart the operation of selecting a point having the maximum medialness.

23. An apparatus which analyzes an object based on a three-dimensional image of the object to be analyzed serving as a cell, a tissue, or an organ having a linear figure, comprising:

a first blurring unit which performs scale-space transformation to the three-dimensional image based on a predetermined first scale $\sigma$;

a first medialness unit which calculates a first medialness for each pixel of the three-dimensional image after the scale-space transformation; and a linear figure fitting unit which calculates a graphic approximated to the linear figure of the object based on the first medialness.

24. A program which makes a computer operate as an apparatus which analyzes an object based on a three-dimensional image of the object to be analyzed serving as a cell, a tissue, or an organ having a linear figure, the program causing the computer to execute:

a first blurring procedure which performs scale-space transformation to the three-dimensional image based on a predetermined first scale $\sigma$;

a first medialness procedure which calculates a first medialness for each pixel of the three-dimensional image after the scale-space transformation; and a linear figure fitting procedure which calculates a graphic approximated to the linear figure of the object based on the first medialness.

25. The apparatus which analyzes a cell, a tissue, or an organ having a linear figure according to claim 24, comprising:

a second blurring unit which performs scale-space transformation to the three-dimensional image based on a predetermined second scale $\sigma$;

a second medialness unit which calculates a product of characteristic values of Hessian tensors as a second medialness for each pixel of the three-dimensional image after the scale-space transformation by the second blurring unit; and a thorn-like portion detecting unit which detects a thorn-like portion present on the linear figure based on the second medialness.

* * * * *